United States Patent [19]
Matsuura et al.

[11] Patent Number: 5,998,223
[45] Date of Patent: *Dec. 7, 1999

[54] METHOD OF ASSAYING AUTOIMMUNE ANTICARDIOLIPIN ANTIBODY AND KIT THEREFOR

[75] Inventors: Eiji Matsuura; Hisato Nagae; Makoto Igarashi; Yoshiko Igarashi, all of Choshi; Takao Koike, Sapporo, all of Japan

[73] Assignee: Yamasa Corporation, Chiba-ken, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/640,977
[22] PCT Filed: Nov. 15, 1994
[86] PCT No.: PCT/JP94/01929
  § 371 Date: May 9, 1996
  § 102(e) Date: May 9, 1996
[87] PCT Pub. No.: WO95/14231
  PCT Pub. Date: May 26, 1995

[30] Foreign Application Priority Data

Nov. 16, 1993 [JP] Japan ................................. 5-309874

[51] Int. Cl.$^6$ ...................... G01N 33/543; G01N 33/549; G01N 33/53; C07K 1/00
[52] U.S. Cl. ...................... 436/518; 436/531; 436/532; 436/808; 435/7.1; 435/7.92; 435/7.94; 435/7.95; 435/970; 435/975; 530/359; 530/380; 530/389.3
[58] Field of Search ...................... 436/518, 531, 436/532, 808; 435/7.1, 7.92, 7.94, 7.95, 970, 975; 530/359, 380, 389.3

[56] References Cited

U.S. PATENT DOCUMENTS 5,344,758  9/1994  Krilis et al. ............................... 433/4.1
5,472,883  12/1995  Matsuura et al. ........................ 436/518
5,506,110  4/1996  Matsuura et al. ....................... 435/7.94

FOREIGN PATENT DOCUMENTS

91/06006  5/1991  WIPO .
93/16387  8/1993  WIPO .

OTHER PUBLICATIONS

Ichikawa et al., "β$_2$-Glycoprotein I Reactivity of Monoclonal Anticardiolipin Antibodies from Patients with the Antiphospholipid Syndrome," Arthritis & Rheumatism, 37(10): 1453–1461, Oct. 9, 1994.

Igarashi et al., "Expression of Anticardiolipin Cofactor, Human β$_2$-Glycoprotein I, by a Recombinant Baculovirus/Insect Cell Septen," Clinical and Experimental Immunology 93(1): 19–25, Jul. 1993.

Mehdi et al.,. Nucleotide Sequence and Expression of the Human Gene Encoding Apolipoprotein H (β–Glycoprotein I) Gene 108: 293–298, 1991.

R. Roubey, "Autoantibodies to Phospholipid–Binding Plasma Proteins . . . " Blood, 84(9) : 2854–2867, Nov. 1, 1994.

Primary Examiner—Nita Minnifield
Assistant Examiner—Padma Baskar
Attorney, Agent, or Firm—Wenderoth, Lind & Ponack, L.L.P.

[57] ABSTRACT

In a method for assaying an anticardiolipin antibody in a sample utilizing β2-glycoprotein I, a polypeptide having the same amino acid sequence as domain IV of β2-glycoprotein I or a polypeptide partially different therefrom but functionally equivalent thereto is used in place of β2-glycoprotein I itself. According to this method, an autoantibody from patients with antiphospholipid syndrome can be accurately assayed in a simple manner.

18 Claims, 19 Drawing Sheets lane 1 ; Serum-derived $\beta_2$-GPI
 2 ; Recombinant $\beta_2$-GPI
     (D I - V, whole)
 3 ; D IV - V
 4 ; D III - V
 5 ; D II - V
 6 ; D I - III
 7 ; D I - IV

FIG. 9

| | Deletion mutant protein | | | | | Epitope |
|---|---|---|---|---|---|---|
| | DIV-V | DIII-V | DII-V | DI-III | DI-IV | |
| Cof-18 | + | + | + | − | − | V |
| Cof-19 | + | + | + | − | − | V |
| Cof-20 | − | + | + | + | + | III |
| Cof-21 | + | + | + | − | + | IV |
| Cof-22 | − | + | + | + | + | III |
| Cof-23 | + | + | + | − | + | IV |

FIG. 12
Non-oxygenated plate
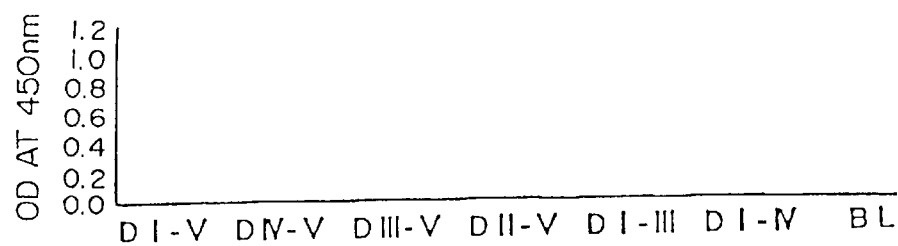
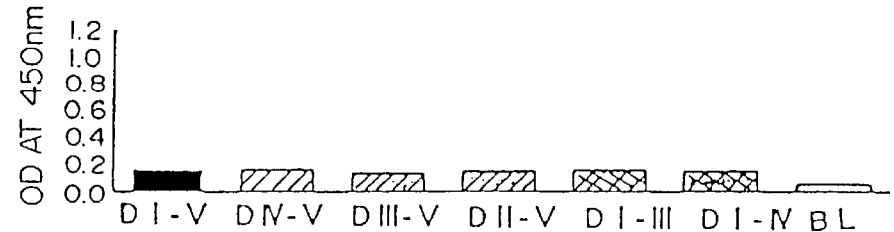

FIG. 13
Non-oxygenated plate
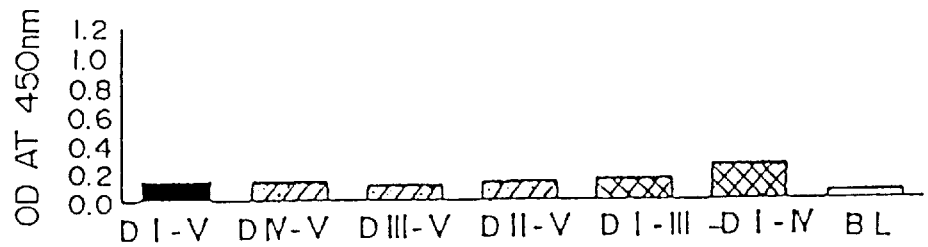
Deletion mutant protein
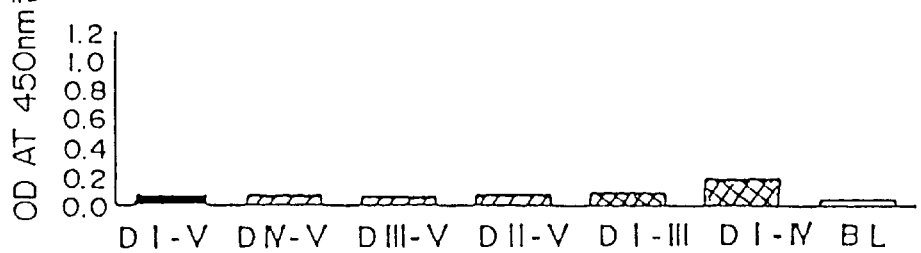
Deletion mutant protein
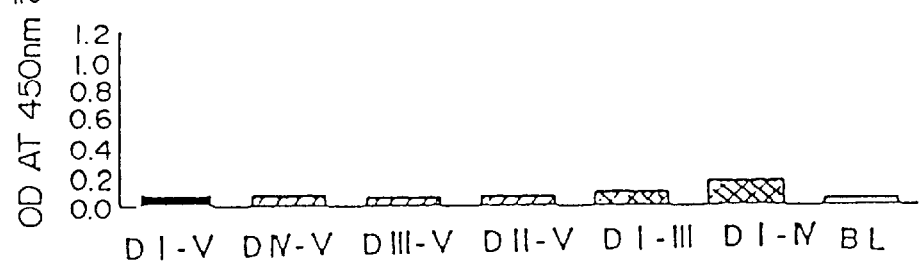
Deletion mutant protein FIG. 14
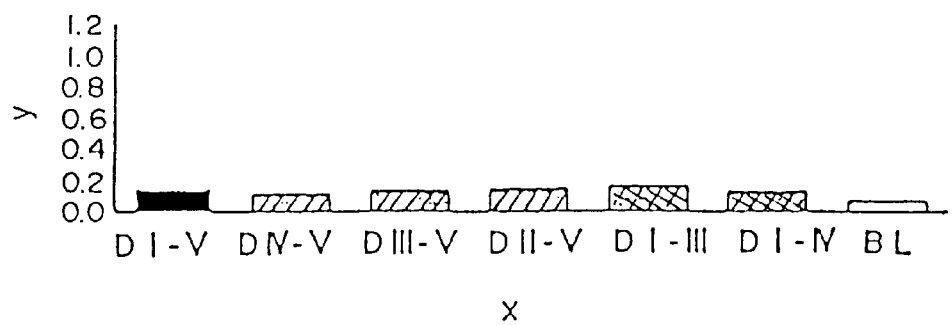
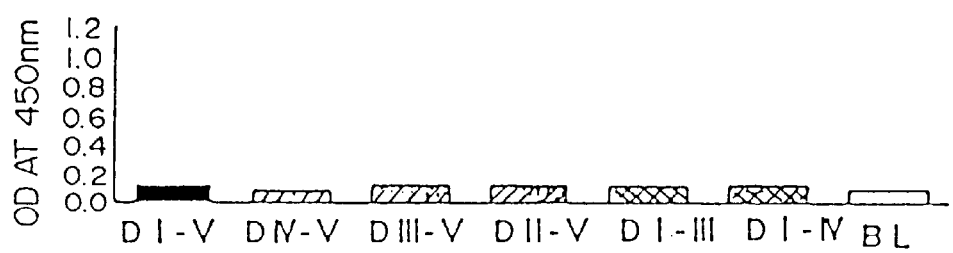
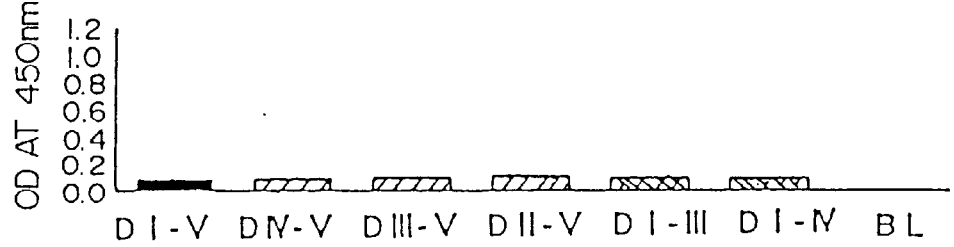

FIG. 15
Poly-oxygenated plate
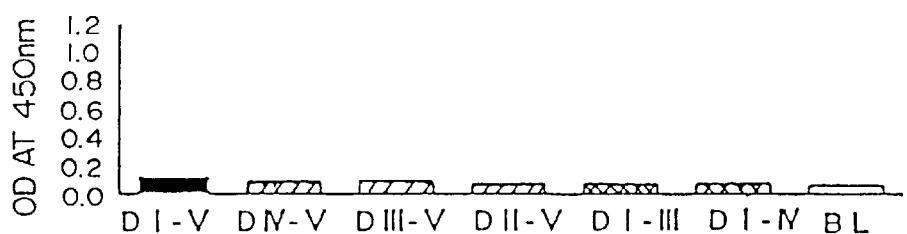
Deletion mutant protein
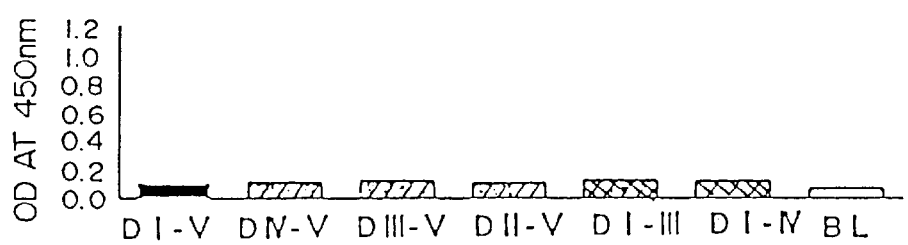
Deletion mutant protein
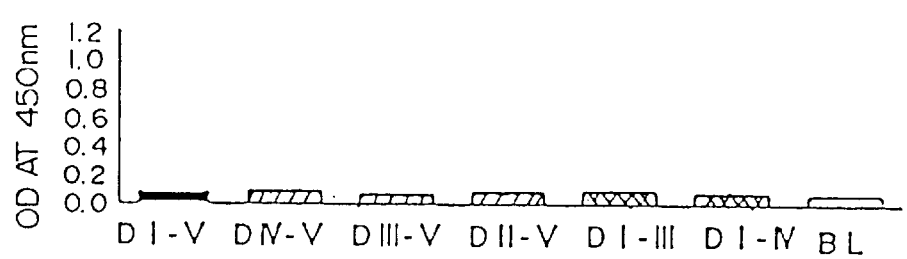
Deletion mutant protein
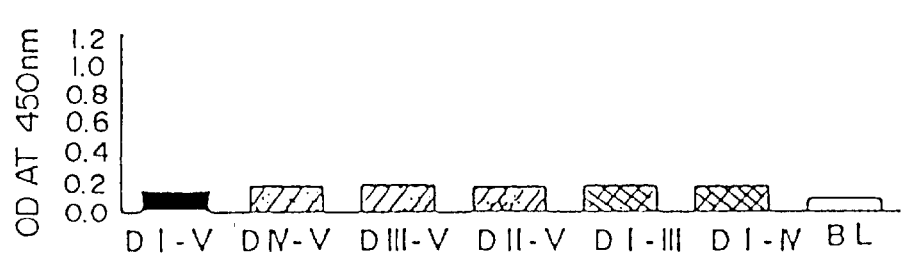
Deletion mutant protein F I G. 16
Poly-oxygenated plate
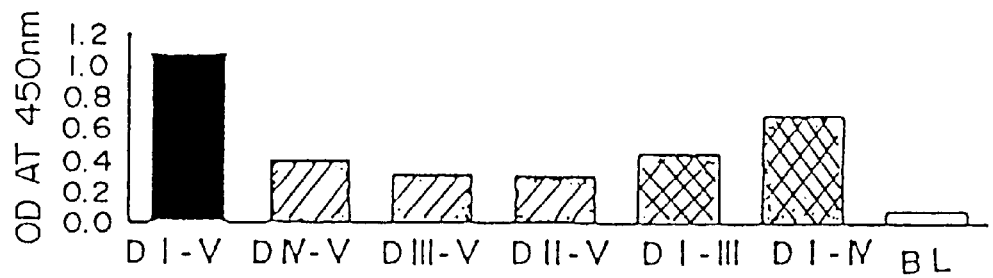
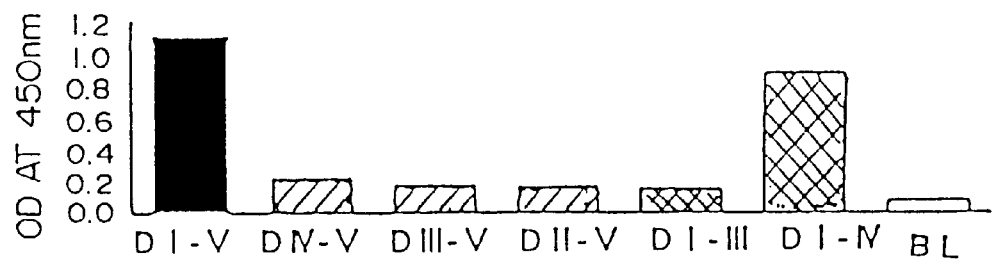
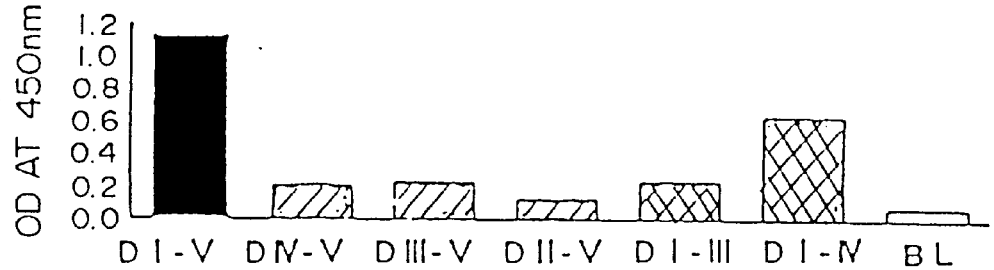

FIG. 17
Poly-oxygenated plate
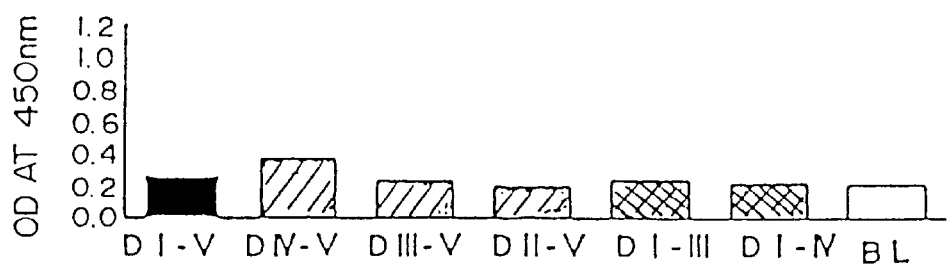
Syphilis #1
Deletion mutant protein
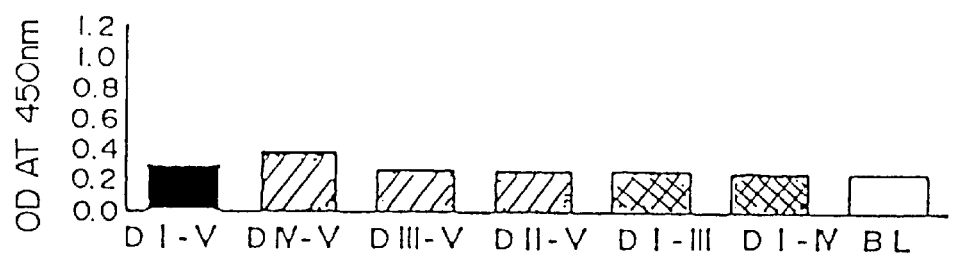
2
Deletion mutant protein
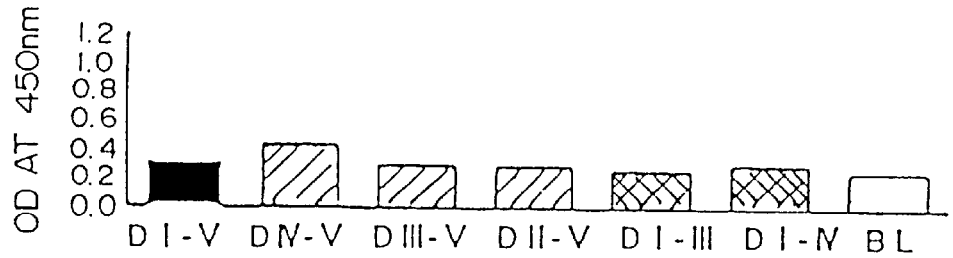
3
Deletion mutant protein

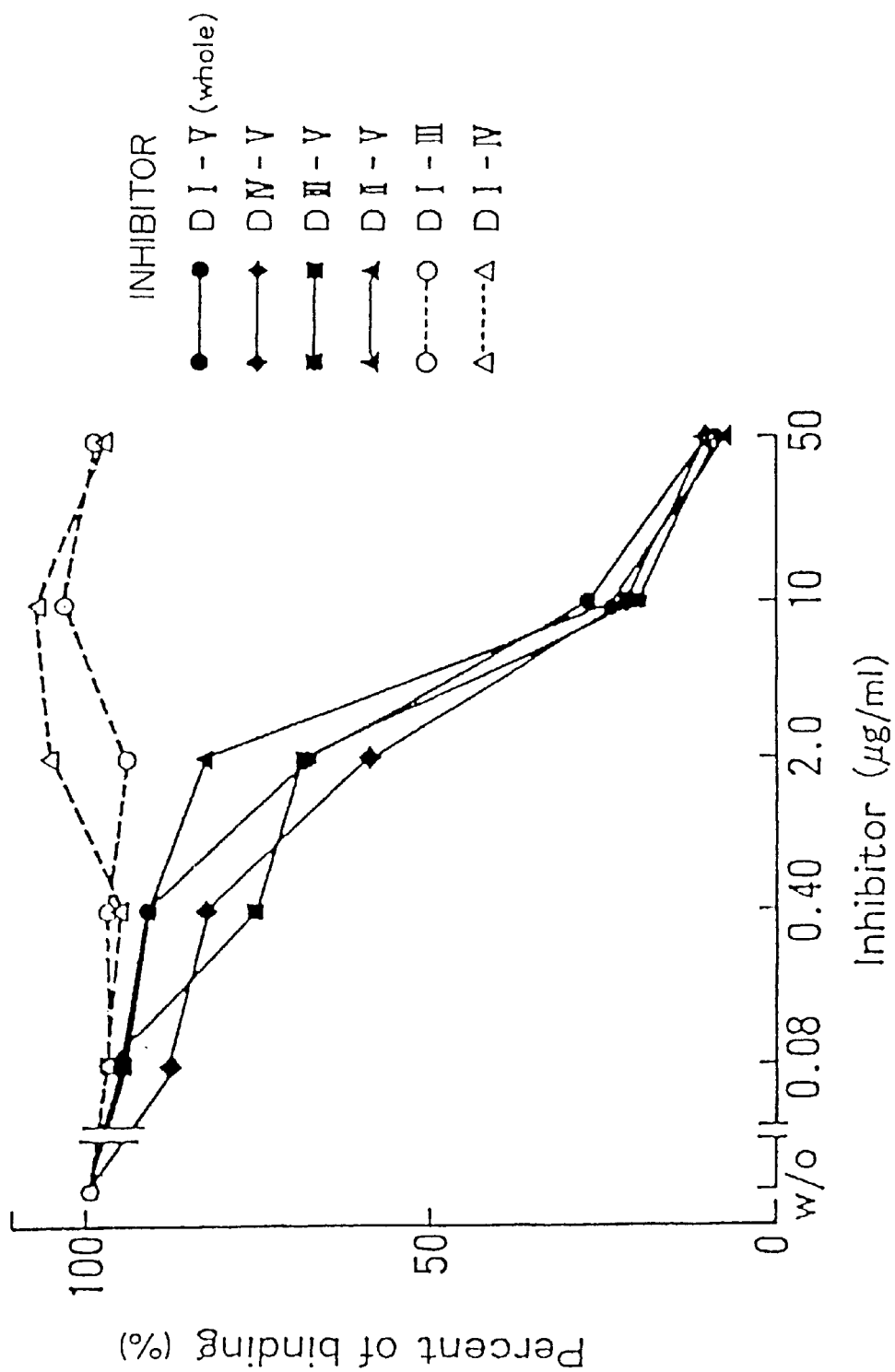

```
                              SEQUENCE LISTING (1) GENERAL INFORMATION:

(iii) NUMBER OF SEQUENCES:  14

(2) INFORMATION FOR SEQ ID NO:1:

(i) SEQUENCE CHARACTERISTICS:
         (A) LENGTH:  326 amino acids
         (B) TYPE:  amino acids
         (C) STRANDEDNESS:  single
         (D) TOPOLOGY:  linear (ii) MOLECULE TYPE: protein (vi) ORIGINAL SOURCE:
         (A) ORGANISM:  Homo sapiens (ix) FEATURE:
         (A) NAME/KEY:   2-glycoprotein (Domains I, II, III, IV and V)
         (B) LOCATION:
         (C) IDENTIFICATION METHOD:
         (D) OTHER INFORMATION:

(xi) SEQUENCE DESCRIPTION: SEQ ID NO:1:

Gly Arg Thr Cys Pro Lys Pro Asp Asp Leu Pro Phe Ser Thr Val
1               5                  10                  15

Val Pro Leu Lys Thr Phe Tyr Glu Pro Gly Glu Glu Ile Thr Tyr
                20                  25                  30

Ser Cys Lys Pro Gly Tyr Val Ser Arg Gly Gly Met Arg Lys Phe
                35                  40                  45

Ile Cys Pro Leu Thr Gly Leu Trp Pro Ile Asn Thr Leu Lys Cys
                50                  55                  60

Thr Pro Arg Val Cys Pro Phe Ala Gly Ile Leu Glu Asn Gly Ala
                65                  70                  75

Val Arg Tyr Thr Thr Phe Glu Tyr Pro Asn Thr Ile Ser Phe Ser
                80                  85                  90

Cys Asn Thr Gly Phe Tyr Leu Asn Gly Ala Asp Ser Ala Lys Cys
                95                  100                 105

Thr Glu Glu Gly Lys Trp Ser Pro Glu Leu Pro Val Cys Ala Pro
                110                 115                 120

Ile Ile Cys Pro Pro Pro Ser Ile Pro Thr Phe Ala Thr Leu Arg
                125                 130                 135

Val Tyr Lys Pro Ser Ala Gly Asn Asn Ser Leu Tyr Arg Asp Thr
                140                 145                 150

Ala Val Phe Glu Cys Leu Pro Gln His Ala Met Phe Gly Asn Asp
                155                 160                 165

Thr Ile Thr Cys Thr Thr His Gly Asn Trp Thr Lys Leu Pro Glu
                170                 175                 180

Cys Arg Glu Val Lys Cys Pro Phe Pro Ser Arg Pro Asp Asn Gly
                185                 190                 195

Phe Val Asn Tyr Pro Ala Lys Pro Thr Leu Tyr Tyr Lys Asp Lys
                200                 205                 210

Ala Thr Phe Gly Cys His Asp Gly Tyr Ser Leu Asp Gly Pro Glu
                215                 220                 225
```

```
Glu Ile Glu Cys Thr Lys Leu Gly Asn Trp Ser Ala Met Pro Ser
                230                 235                 240

Cys Lys Ala Ser Cys Lys Val Pro Val Lys Ala Thr Val Val
                245                 250                 255

Tyr Gln Gly Glu Arg Val Lys Ile Gln Glu Lys Phe Lys Asn Gly
                260                 265                 270

Met Leu His Gly Asp Lys Val Ser Phe Phe Cys Lys Asn Lys Glu
                275                 280                 285

Lys Lys Cys Ser Tyr Thr Glu Asp Ala Gln Cys Ile Asp Gly Thr
                290                 295                 300

Ile Glu Val Pro Lys Cys Phe Lys Glu His Ser Ser Leu Ala Phe
                305                 310                 315

Trp Lys Thr Asp Ala Ser Asp Val Lys Pro Cys
                320                 325

(2) INFORMATION FOR SEQ ID NO:2:

(i) SEQUENCE CHARACTERISTICS:
        (A) LENGTH:  248 amino acids
        (B) TYPE:  amino acids
        (C) STRANDEDNESS:  single
        (D) TOPOLOGY:  linear (ii) MOLECULE TYPE: protein (vi) ORIGINAL SOURCE:
        (A) ORGANISM:  Homo sapiens (ix) FEATURE:
        (A) NAME/KEY:   2-glycoprotein (Domains I, II, III and IV)
        (B) LOCATION:
        (C) IDENTIFICATION METHOD:
        (D) OTHER INFORMATION:

(xi) SEQUENCE DESCRIPTION: SEQ ID NO:2:

Gly Arg Thr Cys Pro Lys Pro Asp Asp Leu Pro Phe Ser Thr Val
1                5                  10                  15

Val Pro Leu Lys Thr Phe Tyr Glu Pro Gly Glu Glu Ile Thr Tyr
                20                  25                  30

Ser Cys Lys Pro Gly Tyr Val Ser Arg Gly Gly Met Arg Lys Phe
                35                  40                  45

Ile Cys Pro Leu Thr Gly Leu Trp Pro Ile Asn Thr Leu Lys Cys
                50                  55                  60

Thr Pro Arg Val Cys Pro Phe Ala Gly Ile Leu Glu Asn Gly Ala
                65                  70                  75

Val Arg Tyr Thr Thr Phe Glu Tyr Pro Asn Thr Ile Ser Phe Ser
                80                  85                  90

Cys Asn Thr Gly Phe Tyr Leu Asn Gly Ala Asp Ser Ala Lys Cys
                95                  100                 105

Thr Glu Glu Gly Lys Trp Ser Pro Glu Leu Pro Val Cys Ala Pro
                110                 115                 120

Ile Ile Cys Pro Pro Pro Ser Ile Pro Thr Phe Ala Thr Leu Arg
                125                 130                 135

Val Tyr Lys Pro Ser Ala Gly Asn Asn Ser Leu Tyr Arg Asp Thr
                140                 145                 150

Ala Val Phe Glu Cys Leu Pro Gln His Ala Met Phe Gly Asn Asp
                155                 160                 165

Thr Ile Thr Cys Thr Thr His Gly Asn Trp Thr Lys Leu Pro Glu
                170                 175                 180

Cys Arg Glu Val Lys Cys Pro Phe Pro Ser Arg Pro Asp Asn Gly
```

```
                    185                 190                 195

Phe Val Asn Tyr Pro Ala Lys Pro Thr Leu Tyr Tyr Lys Asp Lys
                200                 205                 210

Ala Thr Phe Gly Cys His Asp Gly Tyr Ser Leu Asp Gly Pro Glu
                215                 220                 225

Glu Ile Glu Cys Thr Lys Leu Gly Asn Trp Ser Ala Met Pro Ser
                230                 235                 240

Cys Lys Ala Ser Cys Lys Val Pro
                245

(2) INFORMATION FOR SEQ ID NO:3:

(i) SEQUENCE CHARACTERISTICS:
        (A) LENGTH:  181 amino acids
        (B) TYPE:  amino acids
        (C) STRANDEDNESS:  single
        (D) TOPOLOGY:  linear (ii) MOLECULE TYPE:  protein (vi) ORIGINAL SOURCE:
        (A) ORGANISM:  Homo sapiens (ix) FEATURE:
        (A) NAME/KEY:      2-glycoprotein (Domains I, II and III)
        (B) LOCATION:
        (C) IDENTIFICATION METHOD:
        (D) OTHER INFORMATION:

(xi) SEQUENCE DESCRIPTION: SEQ ID NO:3:

Gly Arg Thr Cys Pro Lys Pro Asp Asp Leu Pro Phe Ser Thr Val
1               5                   10                  15

Val Pro Leu Lys Thr Phe Tyr Glu Pro Gly Glu Glu Ile Thr Tyr
                20                  25                  30

Ser Cys Lys Pro Gly Tyr Val Ser Arg Gly Gly Met Arg Lys Phe
                35                  40                  45

Ile Cys Pro Leu Thr Gly Leu Trp Pro Ile Asn Thr Leu Lys Cys
                50                  55                  60

Thr Pro Arg Val Cys Pro Phe Ala Gly Ile Leu Glu Asn Gly Ala
                65                  70                  75

Val Arg Tyr Thr Thr Phe Glu Tyr Pro Asn Thr Ile Ser Phe Ser
                80                  85                  90

Cys Asn Thr Gly Phe Tyr Leu Asn Gly Ala Asp Ser Ala Lys Cys
                95                  100                 105

Thr Glu Glu Gly Lys Trp Ser Pro Glu Leu Pro Val Cys Ala Pro
                110                 115                 120

Ile Ile Cys Pro Pro Pro Ser Ile Pro Thr Phe Ala Thr Leu Arg
                125                 130                 135

Val Tyr Lys Pro Ser Ala Gly Asn Asn Ser Leu Tyr Arg Asp Thr
                140                 145                 150

Ala Val Phe Glu Cys Leu Pro Gln His Ala Met Phe Gly Asn Asp
                155                 160                 165

Thr Ile Thr Cys Thr Thr His Gly Asn Trp Thr Lys Leu Pro Glu
                170                 175                 180

Cys (2) INFORMATION FOR SEQ ID NO:4:

(i) SEQUENCE CHARACTERISTICS:
        (A) LENGTH:  266 amino acids
        (B) TYPE:  amino acids
```

(C) STRANDEDNESS: single
(D) TOPOLOGY: linear (ii) MOLECULE TYPE: protein (vi) ORIGINAL SOURCE:
    (A) ORGANISM: Homo sapiens (ix) FEATURE:
    (A) NAME/KEY: 2-glycoprotein (Domains II, III, IV and V)
    (B) LOCATION:
    (C) IDENTIFICATION METHOD:
    (D) OTHER INFORMATION:

(xi) SEQUENCE DESCRIPTION: SEQ ID NO:4:

```
Thr Pro Arg Val Cys Pro Phe Ala Gly Ile Leu Glu Asn Gly Ala
1               5                   10                  15

Val Arg Tyr Thr Thr Phe Glu Tyr Pro Asn Thr Ile Ser Phe Ser
                20                  25                  30

Cys Asn Thr Gly Phe Tyr Leu Asn Gly Ala Asp Ser Ala Lys Cys
                35                  40                  45

Thr Glu GLu Gly Lys Trp Ser Pro Glu Leu Pro Val Cys Ala Pro
                50                  55                  60

Ile Ile Cys Pro Pro Pro Ser Ile Pro Thr Phe Ala Thr Leu Arg
                65                  70                  75

Val Tyr Lys Pro Ser Ala Gly Asn Asn Ser Leu Tyr Arg Asp Thr
                80                  85                  90

Ala Val Phe Glu Cys Leu Pro Gln His Ala Met Phe Gly Asn Asp
                95                  100                 105

Thr Ile Thr Cys Thr Thr His Gly Asn Trp Thr Lys Leu Pro Glu
                110                 115                 120

Cys Arg Glu Val Lys Cys Pro Phe Pro Ser Arg Pro Asp Asn Gly
                125                 130                 135

Phe Val Asn Tyr Pro Ala Lys Pro Thr Leu Tyr Tyr Lys Asp Lys
                140                 145                 150

Ala Thr Phe Gly Cys His Asp Gly Tyr Ser Leu Asp Gly Pro Glu
                155                 160                 165

Glu Ile Glu Cys Thr Lys Leu Gly Asn Trp Ser Ala Met Pro Ser
                170                 175                 180

Cys Lys Ala Ser Cys Lys Val Pro Val Lys Lys Ala Thr Val Val
                185                 190                 195

Tyr Gln Gly Glu Arg Val Lys Ile Gln Glu Lys Phe Lys Asn Gly
                200                 205                 210

Met Leu His Gly Asp Lys Val Ser Phe Phe Cys Lys Asn Lys Glu
                215                 220                 225

Lys Lys Cys Ser Tyr Thr Glu Asp Ala Gln Cys Ile Asp Gly Thr
                230                 235                 240

Ile Glu Val Pro Lys Cys Phe Lys Glu His Ser Ser Leu Ala Phe
                245                 250                 255

Trp Lys Thr Asp Ala Ser Asp Val Lys Pro Cys
                260                 265
```

(2) INFORMATION FOR SEQ ID NO:5:

(i) SEQUENCE CHARACTERISTICS:
        (A) LENGTH: 207 amino acids
        (B) TYPE: amino acids
        (C) STRANDEDNESS: single
        (D) TOPOLOGY: linear (ii) MOLECULE TYPE: protein (vi) ORIGINAL SOURCE:
    (A) ORGANISM: Homo sapiens (ix) FEATURE:
    (A) NAME/KEY:    2-glycoprotein (Domains III, IV and V)
    (B) LOCATION:
    (C) IDENTIFICATION METHOD:
    (D) OTHER INFORMATION:

(xi) SEQUENCE DESCRIPTION: SEQ ID NO:5:

```
                                        Pro
                                        1
Ile Ile Cys Pro Pro Ser Ile Pro Thr Phe Ala Thr Leu Arg
        5           10              15
Val Tyr Lys Pro Ser Ala Gly Asn Asn Ser Leu Tyr Arg Asp Thr
            20              25              30
Ala Val Phe Glu Cys Leu Pro Gln His Ala Met Phe Gly Asn Asp
            35              40              45
Thr Ile Thr Cys Thr Thr His Gly Asn Trp Thr Lys Leu Pro Glu
            50              55              60
Cys Arg Glu Val Lys Cys Pro Phe Pro Ser Arg Pro Asp Asn Gly
            65              70              75
Phe Val Asn Tyr Pro Ala Lys Pro Thr Leu Tyr Tyr Lys Asp Lys
            80              85              90
Ala Thr Phe Gly Cys His Asp Gly Tyr Ser Leu Asp Gly Pro Glu
            95              100             105
Glu Ile Glu Cys Thr Lys Leu Gly Asn Trp Ser Ala Met Pro Ser
            110             115             120
Cys Lys Ala Ser Cys Lys Val Pro Val Lys Lys Ala Thr Val Val
            125             130             135
Tyr Gln Gly Glu Arg Val Lys Ile Gln Glu Lys Phe Lys Asn Gly
            140             145             150
Met Leu His Gly Asp Lys Val Ser Phe Phe Cys Lys Asn Lys Glu
            155             160             165
Lys Lys Cys Ser Tyr Thr Glu Asp Ala Gln Cys Ile Asp Gly Thr
            170             175             180
Ile Glu Val Pro Lys Cys Phe Lys Glu His Ser Ser Leu Ala Phe
            185             190             195
Trp Lys Thr Asp Ala Ser Asp Val Lys Pro Cys
            200                 205
```

(2) INFORMATION FOR SEQ ID NO:6:

(i) SEQUENCE CHARACTERISTICS:
        (A) LENGTH: 145 amino acids
        (B) TYPE:   amino acids
        (C) STRANDEDNESS: single
        (D) TOPOLOGY:     linear (ii) MOLECULE TYPE: protein (vi) ORIGINAL SOURCE:
        (A) ORGANISM: Homo sapiens (ix) FEATURE:
        (A) NAME/KEY:   2-glycoprotein (Domains IV and V)
        (B) LOCATION:
        (C) IDENTIFICATION METHOD:
        (D) OTHER INFORMATION:

(xi) SEQUENCE DESCRIPTION: SEQ ID NO:6:

Arg Glu Val Lys Cys Pro Phe Pro Ser Arg Pro Asp Asn Gl

```
            1               5                    10
Phe Val Asn Tyr Pro Ala Lys Pro Thr Leu Tyr Tyr Lys Asp Ly
          15                  20                  25

Ala Thr Phe Gly Cys His Asp Gly Tyr Ser Leu Asp Gly Pro Gl
          30                  35              40

Glu Ile Glu Cys Thr Lys Leu Gly Asn Trp Ser Ala Met Pro Se
          45                  50              55

Cys Lys Ala Ser Cys Lys Val Pro Val Lys Lys Ala Thr Val Va
          60                  65              70

Tyr Gln Gly Glu Arg Val Lys Ile Gln Glu Lys Phe Lys Asn Gl
          75                  80                  85

Met Leu His Gly Asp Lys Val Ser Phe Phe Cys Lys Asn Lys Gl
          90                  95                  100

Lys Lys Cys Ser Tyr Thr Glu Asp Ala Gln Cys Ile Asp Gly Th
          105                 110                 115

Ile Glu Val Pro Lys Cys Phe Lys Glu His Ser Ser Leu Ala Ph
          120                 125                 130

Trp Lys Thr Asp Ala Ser Asp Val Lys Pro Cys
          135                 140             145
```

(2) INFORMATION FOR SEQ ID NO:7:

(i) SEQUENCE CHARACTERISTICS:
        (A) LENGTH: 21 bases
        (B) TYPE: nucleic acid
        (C) STRANDEDNESS: single stranded
        (D) TOPOLOGY: linear (ii) MOLECULE TYPE: other nucleic acid (iii) HYPOTHETICAL: no (iv) ANTI-SENSE: no (v) FRAGMENT TYPE: 5'-Primer (xi) SEQUENCE DESCRIPTION: SEQ ID NO:7:

GTAATAAAAA AACCTATAAA T                        21

(2) INFORMATION FOR SEQ ID NO:8:

(i) SEQUENCE CHARACTERISTICS:
        (A) LENGTH: 30 bases
        (B) TYPE: nucleic acid
        (C) STRANDEDNESS: single stranded
        (D) TOPOLOGY: linear (ii) MOLECULE TYPE: other nucleic acid (iii) HYPOTHETICAL: no (iv) ANTI-SENSE: no (v) FRAGMENT TYPE: 3'-Primer (xi) SEQUENCE DESCRIPTION: SEQ ID NO:8:

ACAGAATTCT TAACAACTTG GCATGGCAGA               30

(2) INFORMATION FOR SEQ ID NO:9:

(i) SEQUENCE CHARACTERISTICS:
        (A) LENGTH: 30 bases
        (B) TYPE: nucleic acid
        (C) STRANDEDNESS: single stranded
        (D) TOPOLOGY: linear (ii) MOLECULE TYPE: other nucleic acid (iii) HYPOTHETICAL: no (iv) ANTI-SENSE: no (v) FRAGMENT TYPE: 3'-Primer (xi) SEQUENCE DESCRIPTION: SEQ ID NO:9:

TTTGAATTCT CAGCATTCTG GTAATTTAGT                                               30

(2) INFORMATION FOR SEQ ID NO:10:

(i) SEQUENCE CHARACTERISTICS:
            (A) LENGTH: 24 bases
            (B) TYPE: nucleic acid
            (C) STRANDEDNESS: single stranded
            (D) TOPOLOGY: linear (ii) MOLECULE TYPE: other nucleic acid (iii) HYPOTHETICAL: no (iv) ANTI-SENSE: no (v) FRAGMENT TYPE: 3'-Primer (xi) SEQUENCE DESCRIPTION: SEQ ID NO:10:

GGGAGAATTC CGTCCTGCAA TAGC                                                      24

(2) INFORMATION FOR SEQ ID NO:11:

(i) SEQUENCE CHARACTERISTICS:
            (A) LENGTH: 20 bases
            (B) TYPE: nucleic acid
            (C) STRANDEDNESS: single stranded
            (D) TOPOLOGY: linear (ii) MOLECULE TYPE: other nucleic acid (iii) HYPOTHETICAL: no (iv) ANTI-SENSE: no (v) FRAGMENT TYPE: 3'-Primer (xi) SEQUENCE DESCRIPTION: SEQ ID NO:11:

CCCAGTCACG ACGTTGTAAA                                                           20

(2) INFORMATION FOR SEQ ID NO:12:

(i) SEQUENCE CHARACTERISTICS:
            (A) LENGTH: 27 bases
            (B) TYPE: nucleic acid
            (C) STRANDEDNESS: single stranded
            (D) TOPOLOGY: linear (ii) MOLECULE TYPE: other nucleic acid (iii) HYPOTHETICAL: no (iv) ANTI-SENSE: no (v) FRAGMENT TYPE: 5'-Primer (xi) SEQUENCE DESCRIPTION: SEQ ID NO:12:

ACTCTGAATT CTACACCCAG AGTATGT                                                   27

(2) INFORMATION FOR SEQ ID NO:13:

(i) SEQUENCE CHARACTERISTICS:
            (A) LENGTH: 27 bases

-continued

```
        (B) TYPE:  nucleic acid
        (C) STRANDEDNESS:  single stranded
        (D) TOPOLOGY:  linear (ii) MOLECULE TYPE:  other nucleic acid (iii) HYPOTHETICAL:  no (iv) ANTI-SENSE:  no (v) FRAGMENT TYPE:  5'-Primer (xi) SEQUENCE DESCRIPTION: SEQ ID NO:13:

GTCTGGAATT CCATCATCTG CCCTCCA                                       27

(2) INFORMATION FOR SEQ ID NO:14:

(i) SEQUENCE CHARACTERISTICS:
        (A) LENGTH:  27 bases
        (B) TYPE:  nucleic acid
        (C) STRANDEDNESS:  single stranded
        (D) TOPOLOGY:  linear (ii) MOLECULE TYPE:  other nucleic acid (iii) HYPOTHETICAL:  no (iv) ANTI-SENSE:  no (v) FRAGMENT TYPE:  5'-Primer (xi) SEQUENCE DESCRIPTION: SEQ ID NO:14:

CCGAATTCCA GGGAAGTAAA ATGCCCA                                       27
```

METHOD OF ASSAYING AUTOIMMUNE ANTICARDIOLIPIN ANTIBODY AND KIT THEREFOR

BACKGROUND OF THE INVENTION

1. Field of the Invention

The present invention relates to a method for assaying an antiphospholipid antibody and a kit for use in the method. More particularly, the present invention relates to a method for assaying an antiphospholipid antibody and a kit therefor characterized by using, in place of β2-glycoprotein I, a polypeptide containing the same amino acid sequence as a specific domain of β2-glycoprotein I, or a polypeptide different in the amino acid sequence from the specific domain but functionally equivalent thereto.

2. Description of Related

Various assay methods including radioimmunoassay (RIA) and enzyme-linked immunosorbent assay (ELISA) for an anticardiolipin antibody, which is part of the antiphospholipid family, have been reported by Harris et al., Lancet, iii: 1211, 1983; Koike et al., Clin. Exp. Immunl., 56: 193, 1984; and the like.

However, those methods are not necessarily satisfactory, since they involve problems that an anticardiolipin antibody cannot be quantitatively assayed with a high accuracy, or that an anticardiolipin antibody from patients with infectious diseases cannot be assayed differentially from these patients with antiphospholipid syndrome.

Recently, Matsuura et al. have discovered that an anticardiolipin antibody from patients with antiphospholipid syndrome does not recognize an immobilized cardiolipin but a complex of cardiolipin and β2-glycoprotein I (β2-GPI, also called apolipoprotein H or anticardiolipin cofactor). Further, they have developed a new assay for the antiphospholipid antibody based on the new findings, which can overcome the prior art problems [Lancet, 336: 177, 1990; RINSHO MEN-EKI (Clinical Immunology), 22 (Suppl. 15): 170, 1990; WO 91/06006; and J. Immunol., 148:3855, 1992].

Further studies according to Matsuura et al. have revealed that an autoantibody (hitherto called an anticardiolipin antibody) from patients with antiphospholipid syndrome does not react with cardiolipin itself in the complex of cardiolipin and β2-GPI but recognize an altered β2-GPI, of which structure has been conformationally changed due to interaction with a hydrophobic surface on which an oxygen atom is present, such as a cardiolipin-immobilized plate [J. Exp. Med., 179, 457–462 (1994); and KANSEN, ENSHO, MEN-EKI (Infection, Inflammation and Immunity), 23, 9 (1993)]. When applying this new principle, it is unnecessary to use a phospholipid such as cardiolipin as used in the prior art assays. Thus, Matsuura et al. have developed a new method for assaying an autoantibody from patients with antiphospholipid syndrome using a solid phase reagent wherein β2-GPI alone is immobilized on a carrier with the surface on which a polar group has been introduced (WO 93/16387).

On the other hand, β2-GPI is a known glycoprotein, and its amino acid sequence and nucleotide sequence have been already clarified [Int. Immunol., 3, 1217–1221 (1991); Biochem. J., 277, 387 (1991); and Gene, 108, 293 (1991)]. However, it has been considered that it is difficult to express and produce an active β2-GPI according to a conventional expression system in *E. coli* or yeast, since processing and modification such as a formation of disulfide bond are not correctly proceeded for the following reasons:

(1) a native β2-GPI has eleven cysteine-cysteine (S-S) bonds in the molecule, and has a characteristic primary structure called "sushi domain" composed of five domains as shown on FIG. 1; and (2) a nucleotide sequence encodes β2-GPI as a precursor protein wherein a mature protein additionally has a peptide composed of 19 amino acids at the N-terminus, and such an additional peptide should be cleaved when secreted.

However, Igarashi et al. have recently reported that a baculovirus expression system can overcome the difficulty as discussed above, and that a recombinant β2-GPI produced by the baculovirus expression system can be utilized for an assay of an autoantibody from patients with antiphospholipid syndrome [Clin. Exp. Immunol., 93, 19 (1993); and Japanese Patent Application Serial No. 4-152619].

As stated hereinabove, it has been clarified that β2-GPI is undoubtedly a protein necessarily required for an assay of an autoantibody from patients with antiphospholipid syndrome. Nevertheless, clinical significance of the autoantibody from patients with antiphospholipid syndrome still remains unclear. Accordingly, it is considered as being an important problem to be solved in the future to clarify the reactivity of the autoantibody from patients with antiphospholipid syndrome with β2-GPI, which may result in a clarifying mechanism regarding how antiphospholipid syndrome is a caused, and may result in establishing a more convenient assay system.

SUMMARY OF THE INVENTION

In order to clarify the function of each five domains in β2-GPI molecule in an assay for an autoantibody from patients with antiphospholipid syndrome, the present inventors have prepared a mutant protein wherein a specific domain has been deleted (hereinafter referred to as a "deleted mutant protein" or a "domain deleted mutant protein") and examined the reactivity between the domain deleted mutant protein and the autoantibody. As a result, it has been newly found out that:

(1) a phospholipid binding site is present in the fifth domain (domain V) of β2-GPI as shown in FIG. 1;

(2) an epitope (an antibody recognition site), which an autoantibody from patients with antiphospholipid syndrome recognizes, is present in a region centering around the fourth domain (domain IV);

(3) this epitope is usually cryptic, with domain V binding to a phospholipid or the like, resulting in that the β2-GPI molecule undergoes a conformational change, whereby the epitope is exposed to be recognized by the autoantibody.

Based on these findings, the present inventors made further studies to apply the findings to an assay for the autoantibody from patients with antiphospholipid syndrome. The present invention has thus been accomplished.

Accordingly, the present invention relates to a method for assaying an antiphospholipid antibody in a sample utilizing β2-GPI. The method is characterized by using, in place of β2-GPI itself, a polypeptide containing the same amino acid sequence as domain IV of β2-GPI or a polypeptide partially different therefrom but functionally equivalent thereto. The present invention also relates to a kit for use in the method.

The present invention further relates to a method for assaying an antiphospholipid antibody in a sample utilizing β2-GPI and a solid phase reagent wherein a phospholipid is bound to a carrier, which method is characterized by using, in place of β2-GPI itself, a polypeptide containing the same amino acid sequence as domain IV and V of β2-GPI or a polypeptide partially different therefrom but functionally equivalent thereto, and to a kit for use in the method.

The present invention also relates to a method for assaying an antiphospholipid antibody in a sample utilizing a solid phase reagent wherein β2-GPI is bound to a carrier, which method is characterized by using, in place of β2-GPI itself, a polypeptide containing the same amino acid sequence as domain IV of β2-GPI and not containing the same amino acid sequence as domain V of β2-GPI or a polypeptide partially different therefrom but functionally equivalent thereto, and to a kit for use in the method.

The present invention further relates to a method for assaying an antiphospholipid antibody in a sample utilizing a solid phase reagent wherein β2-GPI is bound to a carrier with the surface on which a polar group has been introduced, which method is characterized by using, in place of β2-GPI itself, a polypeptide containing the same amino acid sequence as domain IV and V of β2-GPI or a polypeptide partially different therefrom but functionally equivalent thereto, and to a kit for use in the method.

BRIEF DESCRIPTION OF THE DRAWINGS

FIG. 9 is results from an analysis for an epitope in β2-GPI for an mouse anti-human β2-GPI monoclonal antibody based on the results shown on FIG. 8.

FIG. 12 shows results from an analysis for an epitope for an anti-CL antibody in normal human sera, according to ELISA using each domain deleted protein and an S-plate.

FIG. 13 shows results from an analysis for an epitope for an anti-CL antibody in sera from patients with systemic lupus erythematodes (SLE), according to ELISA using each domain deleted protein and an S-plate.

FIG. 14 shows results from an analysis for an epitope for an anti-CL antibody in sera from patients with syphilis, according to ELISA using each domain deleted protein and an S-plate.

FIG. 15 shows results from an analysis for an epitope for an anti-CL antibody in normal human sera, according to ELISA using each domain deleted protein and a C-plate.

FIG. 16 shows results from an analysis for an epitope for an anti-CL antibody in sera from patients with SLE, according to ELISA using each domain deleted protein and a C-plate.

FIG. 17 shows results from an analysis for an epitope for an anti-CL antibody in sera from patients with syphilis, according to ELISA using each domain deleted protein and a C-plate.

In FIGS. 10 through 19, BL means a blank test.

FIG. 20 shows results from an analysis for a cardiolipin binding site in β2-GPI, according to a competitive assay using each domain deleted mutant protein and a human serum-derived β2-GPI.

DESCRIPTION OF THE PREFERRED EMBODIMENTS

Hereinafter the present invention is described in more detail.

1) Definition

In the specification, the following technical terms are as defined below, unless otherwise indicated.

The term "antiphospholipid antibody" is used to mean an autoantibody which appears in a serum from patients with antiphospholipid syndrome (an autoimmune disease including representatively systemic lupus erythematodes (SLE), or a group of diseases showing symptoms such as thrombosis, neuropathy, recurrent abortion and thrombothytopenia).

The term "domain of β2-GPI" is used to mean a region having a structurally discrete part in β2-GPI. As shown on FIG. 1, a human β2-GPI has five domains which are called domain I, domain II, domain III, domain IV and domain V successively from the N-terminus.

Figure 1:
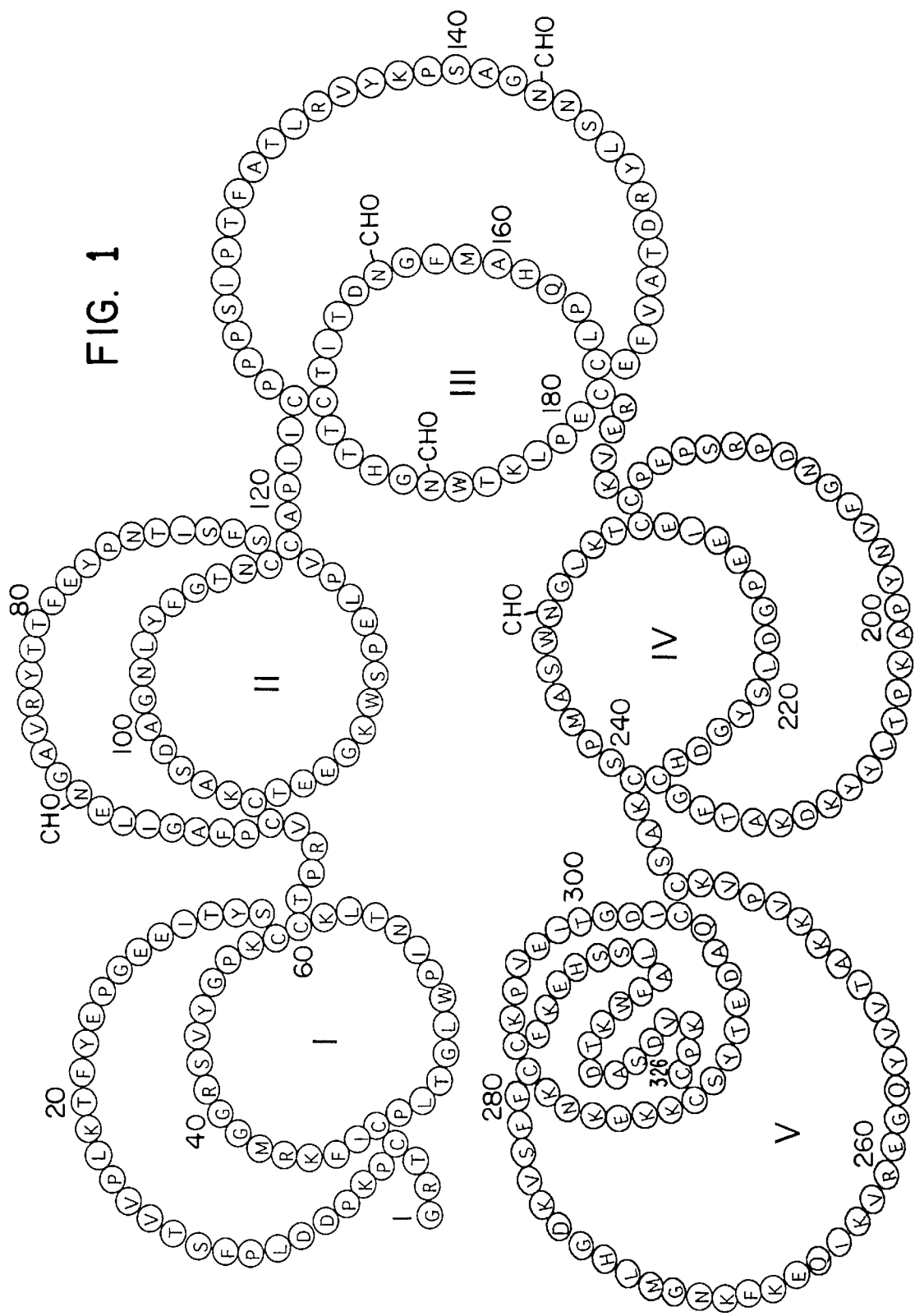
FIG. 1 shows a primary structure of a human serum-derived β2-GPI (I–V) and the location of each domain therein (Seq. ID No. 1).

The term "polypeptide containing the same amino acid sequence as domain IV of β2-GPI" is used to mean, where β2-GPI is derived from human, a polypeptide (or a protein) containing at least the same amino acid sequence as the amino acid sequence from 186 cysteine residue to 241 cysteine residue as shown in FIG. 1.

The term "polypeptide containing the same amino acid sequence as domain IV and V of β2-GPI" is used to mean, where β2-GPI is derived from human, a polypeptide (or a protein) containing at least the same amino acid sequence as the amino acid sequence from 186 cysteine residue to 326 cysteine residue as shown in FIG. 1.

The term "polypeptide containing the same amino acid sequence as domain IV of β2-GPI and not containing the same amino acid sequence as domain V of β2-GPI" is used to mean, where β2-GPI is derived from human, a polypeptide (or a protein) containing at least the same amino acid sequence as the amino acid sequence from 186 cysteine residue to 241 cysteine residue and not containing the same amino acid sequence as the amino acid sequence from 245 cysteine residue to 326 cysteine residue, as shown in FIG. 1.

The term "polypeptide partially different therefrom but functionally equivalent thereto" is used to mean, for example, a polypeptide (or a protein) in which the same amino acid sequence as the domain of a human β2-GPI has been partially modified due to deletion, substitution and/or addition of an amino acid(s), but does not substantially affect on an assay for an antiphospholipid antibody. Representative examples of such a polypeptide include polypeptides having the same amino acid sequence as a specific domain of β2-GPI derived from various animals, especially mammals other than human, e.g., bovine and swine.

2) The Method of the Present Invention and the Kit Therefor

The method of the present invention is an assay for an antiphospholipid antibody in a sample utilizing β2-GPI, which is characterized by using, in place of β2-GPI itself, a polypeptide containing the same amino acid sequence as domain IV of β2-GPI or a polypeptide partially different therefrom but functionally equivalent thereto. More specifically, the method of the present invention is classified into the following three embodiments:

1̂ Method 1:

Method 1 is a method for assaying an antiphospholipid antibody in a sample utilizing β2-GPI and a solid phase reagent wherein a phospholipid is bound to a carrier, which method uses, in place of β2-GPI itself, a polypeptide containing the same amino acid sequence as domain IV and V of β2-GPI or a polypeptide partially different therefrom but functionally equivalent thereto.

2̂ Method 2:

Method 2 is a method for assaying an antiphospholipid antibody in a sample utilizing a solid phase reagent wherein β2-GPI is bound to a carrier, which method uses, in place of β2-GPI itself, a polypeptide containing the same amino acid sequence as domain IV of β2-GPI and not containing the same amino acid sequence as domain V of β2-GPI or a polypeptide partially different therefrom but functionally equivalent thereto.

3̂ Method 3:

Method 3 is a method for assaying an antiphospholipid antibody in a sample utilizing a solid phase reagent wherein β2-GPI is bound to a carrier with the surface on which a polar group has been introduced, which method uses, in place of β2-GPI itself, a polypeptide containing the same amino acid sequence as domain IV and V of β2-GPI or a polypeptide partially different therefrom but functionally equivalent thereto.

(1) Method 1 of the Present Invention and Kit Therefor

Method 1 of the present invention is based on the findings that a phospholipid binding site is present in domain V of β2-GPI; an epitope (an antibody recognition site) which is recognized by an autoantibody from patients with antiphospholipid syndrome is present in a region centering around domain IV; and this epitope is usually cryptic, but domain V binds to a phospholipid or the like, resulting in that the mutant protein undergoes a conformational change, whereby the epitope is exposed to be recognized by the autoantibody. Method 1 is characterized by using a solid phase reagent wherein a phospholipid is bound to a carrier, and a polypeptide containing the same amino acid sequences as domain IV and V of β2-GPI or a polypeptide partially different therefrom but functionally equivalent thereto.

As for the phospholipid, any phospholipid may be used so long as the phospholipid has a negative charge. Examples of the phospholipid include glycerophospholipid such as cardiolipin, phosphatidylserine, phosphatidylinositol and phosphatidylic acid.

The carrier to which the phospholipid is bound is not particularly limited as long as the carrier can accept the binding of the phospholipid thereto. Examples of the carrier are synthetic resins such as polyvinyl chloride, polystyrene, styrene-divinylbenzene copolymer, styrene-maleic anhydride copolymer, nylon, polyacrylamide, polyacrylonitrile, polypropylene, and polymethylene methacrylate. The carrier may take any shape such as plate-like type (e.g. microtiter plate, disk), granular type (e.g., beads), tubular type (e.g., test tube), fibrous type, membrane-like type or fine particulate type (e.g., latex particles). The carrier having an appropriate shape may be chosen depending upon an assay method used.

The phospholipid may be bound to the carrier in a conventional manner which is appropriately chosen from, for example, physical adsorption and ionic bond formation. Preferably, physical adsorption is chosen because of its simplicity.

In Method 1 of the present invention, a polypeptide is used having the same amino acid sequences as domain IV and V of β2-GPI or a polypeptide partially different therefrom but functionally equivalent thereto. In this case, β2-GPI is typically β2-GPI derived from a mammal. A is a human β2-GPI as shown in FIG. 1 is particularly preferred.

The polypeptide may be obtained by synthesizing a gene bearing a necessary domain of a human β2-GPI by a polymerase chain reaction (PCR), integrating the synthesized gene into a baculovirus DNA to construct a recombinant virus and transfecting the recombinant virus into an insect cell to produce the objective polypeptide (protein) therein.

A cDNA library of a human β2-GPI may be prepared in a conventional manner using HepG2 cell which is a human hepatic cancer cell. The cDNA library of HepG2 cell is commercially available, and such a library may be used as a starting material (Brochure No. 935202; manufactured by Stratagene Inc., sold by Funakoshi Co., Ltd.). Furthermore, the full-length nucleotide sequence of a human β2-GPI cDNA has been already reported (Int. Immunol., 3, 1217–1221 (1991), Biochem. J., 277, 387 (1991), Gene, 108, 293 (1991), as described hereinbefore, and the cDNA may therefore be chemically synthesized based on the reported nucleotide sequence.

Using such a human β2-GPI cDNA, a gene containing at least domain IV and V is prepared by PCR. It is well known in the art to prepare a gene amplified by PCR and a specific example thereof will be hereinafter described in Examples. When the prepared gene does not contain a translation initiation codon and/or a translation termination codon, these codons may be artificially inserted into the gene.

Expression of the prepared gene in a baculovirus may be conducted by appropriately choosing and applying a known method. That is, the prepared gene is placed under expression control of a baculovirus gene to construct a recombinant baculovirus which may be employed as an expression viral vector.

Any virus may be used to construct the recombinant baculovirus so long as the virus is classified into a baculovirus. Preferred example of the virus include nuclear polyhederosis viruses such as *Autographa californica* (ATCC VR-1344, hereinafter abbreviated as AcNPV) and *Bombyx mori*.

Baculovirus has a long chain viral DNA (for example, viral DNA of AcNPV has about 130 Kb). It is thus difficult to construct an expression viral vector by directly inserting a gene to be expressed downstream of an expression control region such as promoter in a baculovirus DNA. Accordingly, firstly a viral DNA fragment bearing a gene expression control region is cut out from a baculovirus DNA, then cloned into a plasmid requiring *E. coli* as a host to construct a transfer vector. Secondly, a DNA fragment bearing a gene to be expressed is inserted into the transfer vector at an appropriate site under the expression control region in the baculovirus gene. The constructed transfer vector is then co-transfected into an insect cell together with a wild type baculoviral DNA to cause homologous recombination in the insect cell, resulting in the construction of a recombinant baculovirus in which the gene bearing the desired domain has been inserted under the expression control region in the baculoviral gene.

The transfer vector, which is used to construct the recombinant baculovirus, should contain at least a region required for homologous recombination, a gene expression control region and a cloning site.

The region required for homologous recombination is not particularly limited so long as the region has a function to cause homologous recombination. In general, a part of the DNA sequence of baculovirus or a region corresponding thereto may be employed. Preferably, the region should not affect the virus proliferation even if the region is inactivated by insertion of other DNA fragments therein. As such a DNA region which is non-essential for baculovirus proliferation, a region of polyhedrine gene [Science, 219, 715–721 (1983)] may be exemplified. The polyhedrin gene may be arranged to be placed, for example, at both sides of the cloning site in the recombinant virus, so as to cause homologous recombination.

The gene expression control region is not particularly limited as long as the objective gene can be expressed after the recombinant baculovirus has been transfected to an insect cell. For this purpose, a region may be employed containing a promoter selected from various promoters such as a promoter of a polyhedrin gene of baculovirus, a promoter of a 10× polypeptide gene and a promoter of a basic protein gene. When the promoter of a polyhedrin gene is used as the gene expression control region, it is preferred for a higher expression level to use a region which contains, in addition to the promoter, a part of complete 5' non-translated region including an initiation codon and which does not contain all the 3'-superfluous polyhedrin gene downstream of the initiation codon [J. Gen. Virol., 68, 1233–1250 (1987); and Japanese Patent KOKAI (Laid-Open) No. 1-285198].

The cloning site is required for inserting the DNA fragment to be expressed at an appropriate site downstream of the gene expression control region containing a promoter. For example, the cloning site may be constructed by placing an appropriate linker bearing a restriction recognition sequence at an appropriate site downstream of the gene expression control region.

Preferred examples of the transfer vector which satisfies conditions as described above include pAc373 and pAcYM1. Particularly, pAcYM1 is preferred. These transfer vectors may be constructed in a conventional manner as described in, for example, Japanese patent KOKAI (Laid-Open) No. 1-285198; Mol. Cell. Biol., 3, 2156 (1983); Proc. Natl. Acad. Sci. U.S.A., 82, 8404 (1985); Nature, 315, 592 (1985), J. Gen. Virol., 68, 1233–1250 (1987); Bio/Technology, 6, 47 (1988); and JIKKEN IGAKU (Experimental Medicine), vol. 7, 146 (1989).

After the gene prepared by PCR as described before is inserted into the transfer vector, the obtained transfer vector DNA is co-transfected into an insect cell together with a wild type baculoviral DNA. The co-transfected insect cell is screened for whether it has the DNA fragment to be expressed under the expression control region of baculoviral gene, to obtain the desired recombinant baculovirus.

As the wild type baculovirus, the same virus as that used to construct the transfer vector may be used, and the wild type baculoviral DNA may be prepared from the wild type baculovirus in a conventional manner. For conveniently screening for the recombinant virus, it is preferred to use a wild type baculoviral DNA wherein a lacZ gene encoding β-galactosidase has been previously inserted at the homologous recombination site of the viral DNA. Such a lacZ gene-inserted viral DNA is already commercially available (from, for example, Pharmingen) and may be employed for the above purpose.

The cell to be co-transfected with the baculoviral DNA and the transfer vector DNA is appropriately chosen depending upon virus used. In the case of using, for example, AcNPV as a virus, army worm derived cell (*Spodoptera frugiperda* cell) may be used.

The co-transfection and screening for the recombinant baculovirus may be carried out in a conventional manner, as described in, for example, Texas Agricultural Experiment Station Bulletin No. 1555, Texas A & M University (1987); and Japanese Patent KOKAI (Laid-Open) Nos. 60-37988 and 61-5787.

The constructed recombinant baculovirus is transfected into an insect cell, then the cell is cultured, and the objective polypeptide (protein) is obtained from the culture.

The cell to be transfected with the recombinant baculovirus is not particularly limited so long as the recombinant baculovirus is capable of proliferating in the cell after transfected thereinto. Where the recombinant baculovirus is constructed from AcNPV, army worm derived cell (*Spodoptera frugiperda* cell) is preferably used as the cell to be transfected with the recombinant virus.

As a medium used to culture the cell, media conventionally used for insect cells may be used, and examples of media include Grace medium, Sf-900 medium and EX cell 400 medium. Either a serum-containing medium or a serum-free medium may be used. For easy purification of the objective polypeptide, it is preferred to use a serum-free medium all through the beginning of the culture or to use a serum-containing medium at the start of the culture, then change to a serum-free medium about 24 hours after the start of the culture.

The cell transfected with the recombinant baculovirus may be cultured in a conventional manner, for example, for a time period (60 to 72 hours) sufficient for the polypeptide to be expressed at 20 to 30° C.

The objective polypeptide may be isolated from the cultured medium by appropriately combining procedures conventionally used for purification of a protein. Among them, an affinity chromatography using an anti-β2-GPI antibody or a phospholipid such as cardiolipin is particularly effective for purifying the objective polypeptide.

Method 1 of the present invention is characterized by using the obtained polypeptide having the same amino acid sequence as domain IV and V of β2-GPI and a solid phase reagent wherein a phospholipid is bound to a carrier. Therefore, as long as the solid phase reagent and the polypeptide are used, determination methods, determination conditions and the like used for the assay are not particularly restricted.

For example, when the assay method used in the present invention is classified in terms of the reaction mode, there are known a competitive reaction method and a non-competitive reaction method. In the present invention, any of these methods may be applied. When classified in terms of the detection mode, there are known a non-labelling method (e.g., nephelometry) for directly detecting results of an antigen-antibody reaction, and a labelling method for detecting the results using a marker. Any of these methods may be applied to the present invention. Furthermore, a heterogeneous method requiring BF separation and a homogeneous method not requiring any BF separation are also known, and any of those methods may be applied to the present invention. That is, an assay method which is suitable for the purpose of the present invention may be appropriately chosen from any of these known conventional methods.

Details of those conventional methods are described in, for example, the following articles:

(1) "RADIOIMMUNOASSAY, Second Series" edited by Hiroshi Irie, published May 1, 1979 by Kodansha Publishing Co., Ltd.;
(2) "KOUSO MENEKI SOKUTEIHO (ENZYME IMMUNOASSAY) (second edition)" edited by Eiji Ishikawa et al., published Dec. 15, 1982 by Igaku-Shoin Publishing Co., Ltd.;
(3) RINSHO-BYORI (Clinical Pathology), extra special issue No. 53 "Immunoassay for clinical inspection —technique and application—", published by RINSHO BYORI KANKOKAI, 1983;
(4) "Dictionary of Biotechnology", published Oct. 9, 1986 by CMC Publishing Co., Ltd.;
(5) "Methods in ENZYMOLOGY Vol. 70" (Immunochemical techniques (Part A));
(6) "Methods in ENZYMOLOGY Vol. 73" (Immunochemical techniques (Part B));
(7) "Methods in ENZYMOLOGY Vol. 74" (Immunochemical techniques (Part C));
(8) "Methods in ENZYMOLOGY Vol. 84" (Immunochemical techniques (Part D: Selected Immunoassay)); and
(9) "Methods in ENZYMOLOGY Vol. 92" (Immunochemical techniques (Part E: Monoclonal Antibodies and General Immunoassay Methods)).

(Articles (5)–(9) were published by Academic Press)

Method 1 of the present invention is described below in more detail, taking ELISA as one example.

Firstly, the polypeptide containing the same amino acid sequence as domain IV and V of β2-GPI is reacted with a phospholipid which has been bound to each well of a plate. Then a sample solution (e.g., blood, and serum) is added to each well of the plate, whereby the polypeptide is reacted with antibodies in the sample solution. Secondly, after washing the wells, an enzyme-labelled anti-immunoglobulin antibody (e.g., a peroxidase-labelled anti-IgG antibody) is reacted with the resulting complex, followed by separation of the solid phase from the liquid phase. After a substrate (e.g., hydrogen peroxide and tetramethylbenzidine, when peroxidase is used as a label) is added to the solid phase or the liquid phase, the enzyme activity in either the solid phase or liquid phase is determined. Finally, an amount of the antibodies in the sample is calculated from the obtained measurement data based on a calibration curve previously prepared.

Alternatively, the polypeptide used for the reaction may be added to each well of the plate simultaneously with the sample solution.

The kit of the present invention for use in Method 1 of the present invention is also characterized in that the kit comprises as constituent reagents the solid phase reagent wherein a phospholipid is bound to a carrier and the polypeptide containing the same amino acid sequence as domain IV and V of β2-GPI. Other constituent reagents may be appropriately chosen and used in combination so as to be more suitable for the assay method used.

For example, the kit for performing ELISA as described above may comprise the following reagents:
1̂ a solid phase reagent wherein a phospholipid is bound to a carrier;
2̂ a polypeptide containing the same amino acid sequence as domain IV and V of β2-GPI;
3̂ an enzyme-labeled anti-immunoglobulin antibody;
4̂ a substrate solution; and,
5̂ a standard antibody solution having a known concentration.

(2) Method 2 of the Present Invention and Kit in use Therefor

Method 2 of the present invention is based on the findings that an epitope (an antibody recognition site) which is recognized by an autoantibody from patients with antiphospholipid syndrome is present in a region centering around domain IV; and that domain V is not necessarily required for assaying the autoantibody. Method 2 is characterized by using a solid phase reagent wherein the polypeptide containing the same amino acid sequence as domain IV of β2-GPI and not containing the same amino acid sequence as domain V of β2-GPI or a polypeptide partially different therefrom but functionally equivalent thereto is bound to a carrier.

In Method 2, the polypeptide containing the same amino acid sequence as domain IV of β2-GPI and not containing the same amino acid sequence as domain V of β2-GPI or a polypeptide partially different therefrom but functionally equivalent thereto is used. In this case, β2-GPI may be typically β2-GPI derived from mammal. A human β2-GPI shown in FIG. 1 may be used as a particularly preferred example of β2-GPI.

The polypeptide may be obtained in the same way as in Method 1 of the present invention, that is, by synthesizing a gene bearing a necessary domain in a human β2-GPI by PCR, integrating the synthesized gene into a baculovirus to construct a recombinant virus and transfecting the recombinant virus into an insect cell thereby to produce the objective polypeptide (protein) therein.

The carrier to which the polypeptide is bound is not particularly limited as long as the carrier can accept the binding of the polypeptide thereto. Examples of the carrier are synthetic resins such as polyvinyl chloride, polystyrene, styrene-divinylbenzene copolymer, styrene-maleic anhydride copolymer, nylon, polyacrylamide, polyacrylonitrile, polypropylene, and polymethylene methacrylate.

The carrier as described above may have a polar group introduced on the surface thereof. Herein, the polar group is preferably a group containing an oxygen atom such as hydroxy, carboxyl, carbonyl, formyl, imino and oxygen radicals.

The carrier may be prepared by chemically introducing the polar group into a synthetic resin having a highly protein-adsorbable hydrophobic surface, more specifically, a synthetic resin such as polyvinyl chloride, polystyrene, styrene-divinylbenzene copolymer, styrene-maleic anhydride copolymer, nylon, polyacrylamide, polyacrylonitrile, polypropylene, and polymethylene methacrylate. For preparing the carrier, the following methods may also be used;
a method which comprises exposing the synthetic resins having a hydrophobic surface as described above to UV ray, radiations (e.g., x-ray, β-ray, and γ-ray), electron beams (e.g., protons, and α particles) or the like; and a method which comprises treating with ozone the synthetic resins having a hydrophobic surface as described above.

Examples of such a carrier having a polar group introduced on the surface thereof include EB Plate (Labsystems Co., Ltd.), H Type Plate and C Type Plate (Sumitomo Bakelite Co., Ltd.), Maxi-Soap Plate (Nunc Co., Ltd.), and the like.

The carrier may take any shapes such as plate-like type (e.g., microtiter plate, and disk), granular type (e.g., beads), tubular type (e.g., test tube), fibrous type, membrane-like type, fine particulate type (e.g., latex particles) and the like. The carrier having an appropriate shape may be chosen depending upon the assay method used.

The binding of the polypeptide to such a carrier may be effected in a conventional manner, which may be appropriately chosen from, for example, physical adsorption and ionic bond formation, preferably physical adsorption because of its simplicity.

Method 2 of the present invention is characterized by using the prepared solid phase reagent wherein the polypeptide containing the same amino acid sequence as domain IV of β2-GPI and not containing the same amino acid sequence as domain V of β2-GPI or a polypeptide partially different therefrom but functionally equivalent thereto is bound to a carrier. Therefore, as far as such a solid phase reagent is used, determination methods, determination conditions and the like for the assay are not particularly restricted.

Method 2 of the present invention is described below in more detail, taking ELISA as one example. Firstly, a sample solution (e.g., blood, serum) is added to each well of a plate having bound thereto the polypeptide containing the same amino acid sequence as domain IV of β2-GPI and not containing the same amino acid sequence as domain V, whereby the polypeptide is reacted with antibodies in the sample solution. Secondly, after washing the wells, an enzyme-labelled anti-immunoglobulin antibody (e.g., peroxidase-labelled anti-IgG antibodies) is reacted with the resulting complex, followed by separation of the solid phase from the liquid phase. After a substrate (e.g., hydrogen peroxide and tetramethylbenzidine, when peroxidase is used as a label) is added to the solid phase or the liquid phase, the enzyme activity in either the solid phase or liquid phase is determined. Finally, an amount of the antibodies in the sample is calculated from the obtained measurement data based on a calibration curve previously prepared.

The kit of the present invention for use in Method 2 of the present invention is also characterized in that the kit comprises as a constituent reagent the solid phase reagent wherein the polypeptide containing the same amino acid sequence as domain IV of β2-GPI and not containing the same amino acid sequence as domain V of β2-GPI is bound to a carrier. Other constituent reagents may be appropriately chosen and used in combination so as to be more suitable for the assay method used.

For example, the kit for performing ELISA as described above may comprise the following reagents:

1̂ a solid phase reagent wherein the polypeptide containing the same amino acid sequence as domain IV of β2-GPI and not containing the same amino acid sequence as domain V of β2-GPI is bound to a carrier;

2̂ an enzyme-labeled anti-immunoglobulin antibody;

3̂ a substrate solution; and,

4̂ a standard antibody solution having a known concentration.

(3) Method 3 of the Present Invention and Kit Therefor

Method 3 of the present invention is based on the findings that a phospholipid binding site is present in domain V of β2-GPI; an epitope (an antibody recognition site) which is recognized by an autoantibody from patients with antiphospholipid syndrome is present in a region centering around domain IV; this epitope is usually cryptic, but domain V binds to a phospholipid or the like, resulting in that the mutant protein undergoes a conformational change, whereby the epitope is exposed to be recognized by the autoantibody; and that a carrier with the surface on which a polar group has been introduced can be used in place of the phospholipid. Method 3 is characterized by using a solid phase reagent wherein the polypeptide containing the same amino acid sequence as domain IV and domain V of β2-GPI or a polypeptide partially different therefrom but functionally equivalent thereto is bound to a carrier with a surface on which a polar group has been introduced.

In Method 3 of the present invention, the polypeptide having the same amino acid sequence as domain IV and domain V of β2-GPI is used. In this case, β2-GPI may be typically β2-GPI derived from mammal. Particularly preferred is a human β2-GPI shown in FIG. 1.

The polypeptide may be obtained in the same way as in Method 1 of the present invention, that is, by synthesizing a gene bearing a necessary domain of a human β2-GPI by PCR, integrating the synthesized gene into a baculovirus to construct a recombinant virus and transfecting the recombinant virus into an insect cell thereby to produce the objective polypeptide (protein) therein.

The carrier to which the polypeptide is bound is not particularly limited as long as the carrier has the polar group introduced on the surface thereof.

The carrier may take any one of shapes such as plate-like type (e.g., microtiter plate, and disk), granular type (e.g., beads), tubular type (e.g., test tube), fibrous type, membrane-like type, fine particulate type (e.g., latex particles) and the like. The carrier having an appropriate shape may be chosen depending upon the assay method used.

The binding of the polypeptide to such a carrier may be effected in a conventional manner, which is appropriately chosen from, for example, physical adsorption and ionic bond formation, preferably physical adsorption because of its simplicity.

Method 3 of the present invention is characterized by using the obtained solid phase reagent wherein the polypeptide containing the same amino acid sequence as domain IV and domain V of β2-GPI is bound to a carrier with a surface on which a polar group has been introduced. Therefore, as far as such a solid phase reagent is used, determination methods, determination conditions and the like used for the assay are not particularly restricted.

Method 3 of the present invention is described below in more detail, taking ELISA as one example. Firstly, a sample solution (e.g., blood, serum) is added to each well of a plate having a polar group introduced on the surface thereof and having bound thereto the polypeptide containing the same amino acid sequence as domain IV and domain V of β2-GPI, whereby the polypeptide is reacted with antibodies in the sample solution. Secondly, after washing the wells, an enzyme-labelled anti-immunoglobulin antibody (e.g., peroxidase-labelled anti-IgG antibodies) is reacted with the resulting complex, followed by separation of the solid phase from the liquid phase. After a substrate (e.g., hydrogen peroxide and tetramethylbenzidine, when peroxidase is used as a label) is added to the solid phase or the liquid phase, the enzyme activity in either the solid phase or liquid phase is determined. Finally, an amount of the antibodies in the sample is calculated from the obtained measurement data based on a calibration curve previously prepared.

The kit of the present invention for use in Method 3 is also characterized in that the kit comprises, as a constitution reagent, the solid phase reagent wherein the polypeptide containing the same amino acid sequence as domain IV and domain V of β2-GPI is bound to the carrier with a surface on which a polar group has been introduced. Other constituent reagents may be appropriately chosen and used in combination so as to be more suitable for the assay method used.

For example, the kit for performing ELISA as described above may comprise the following reagents:

1) a solid phase reagent wherein the polypeptide containing the same amino acid sequence as domain IV and domain V of β2-GPI is bound to a carrier with the surface on which a polar group has been introduced;
2) an enzyme-labeled anti-immunoglobulin antibody;
3) a substrate solution; and,
4) a standard antibody solution having a known concentration.

EXAMPLES

Hereinafter the present invention is more specifically described by referring to Examples.

(1) Preparation of a Gene Lacking a Domain at the C-Terminal Region

Using PCR, human β2-GPI genes lacking various domains were synthesized. The synthesized gene was integrated into a baculovirus DNA to construct a recombinant virus. The recombinant virus was transfected into an insect cell to produce the desired domain deleted mutant protein.

To produce a gene lacking the fifth domain (domain V), a primer for PCR is designed at a first step. In this embodiment, a human β2-GPI gene used as a template is inserted into a transfer vector (pAcYM1) at the BamHI site, which is then used to construct a recombinant virus in a baculovirus expression system. Therefore, a sequence, which is located upstream of the 5' non-translated region of the human β2-GPI gene and which is located just upstream of a polyhedrine initiation codon present in the transfer vector, was used as a 5'-primer.

As a result, the sequence of the 5'-primer is as shown below, places the BamHI site at one side (5'-end of the objective gene) of the DNA fragment amplified by PCR.

5'-GTAAT AAAAA AACCT ATAAA T-3' (SEQ ID NO:7 )

As shown in FIG. 1, a human β2-GPI protein forms a secondary structure like a rolled sushi from two internal S-S bridges in the domain molecules (three S-S bonds in domain V only) so that the domain unit can be separated by every S-S bridge. Accordingly, for designing the 3'-primer, a sequence complementary to a region from the end of domain IV to the head of domain V was utilized, that is, a nucleotide sequence complementary to 30 nucleotide sequence from nucleotide +763 to nucleotide +792, when A in the initiation codon ATG was considered as being nucleotide +1. Furthermore, a termination codon was provided after the last cysteine in domain IV so that the translation may be terminated with the codon, and at the same time, the EcoRI site was placed just downstream of the termination codon so that the resulting gene may be readily cloned into a transfer vector. As a result, the sequence of 3'-primer is as given below, and the DNA fragment amplified by PCR can be cut out with BamHI and EcoRI.

5'-ACAGA ATTCT TAACA ACTTG GCATG
    GCAGA-3' (SEQ ID NO:8)

The above two primers chemically synthesized were used to perform PCR using β2-GPI gene-inserted pAcYM1 as templates. A kit for PCR is commercially available (GeneAmp™ PCR Reagent Kit with AmpliTaq™ DNA Polymerase, sold by Takara Shuzo Co., Ltd., manufactured by Hoffman-La Roche Inc.). The actual procedures were made following the protocol attached to the kit.

The amplified DNA fragment was separated by electrophoresis on 0.9% agarose gel. The DNA fragment was recovered and purified from the agarose slice. The objective DNA fragment may be recovered from the agarose slice by freezing and thawing the slice and recovering the aqueous solution exudated from the slice. Several kits for recovering a DNA fragment from an agarose slice are commercially available (DNACELL, manufactured by Kusano Kagaku Kiki Seisakusho, sold by Dai-ichi Kagaku Yakuhin K.K., GENECLEAN II, and Funakoshi K.K.), and the desired DNA fragment may be recovered and purified using these kits.

Since the end of the DNA fragment amplified by PCR is not blunt usually and A is protruded at the 3'-end, the end was filled up with a kit using T4 DNA polymerase (DNA Blunting Kit, Takara Shuzo Co., Ltd.).

The DNA fragment with the blunt end was ligated with pUC118 fragment previously digested with SmaI to be cloned into pUC118 at the SmaI site. The ligation was carried out by a kit using T4 ligase (DNA Ligation Kit, Takara Shuzo Co., Ltd.).

Figure 2:
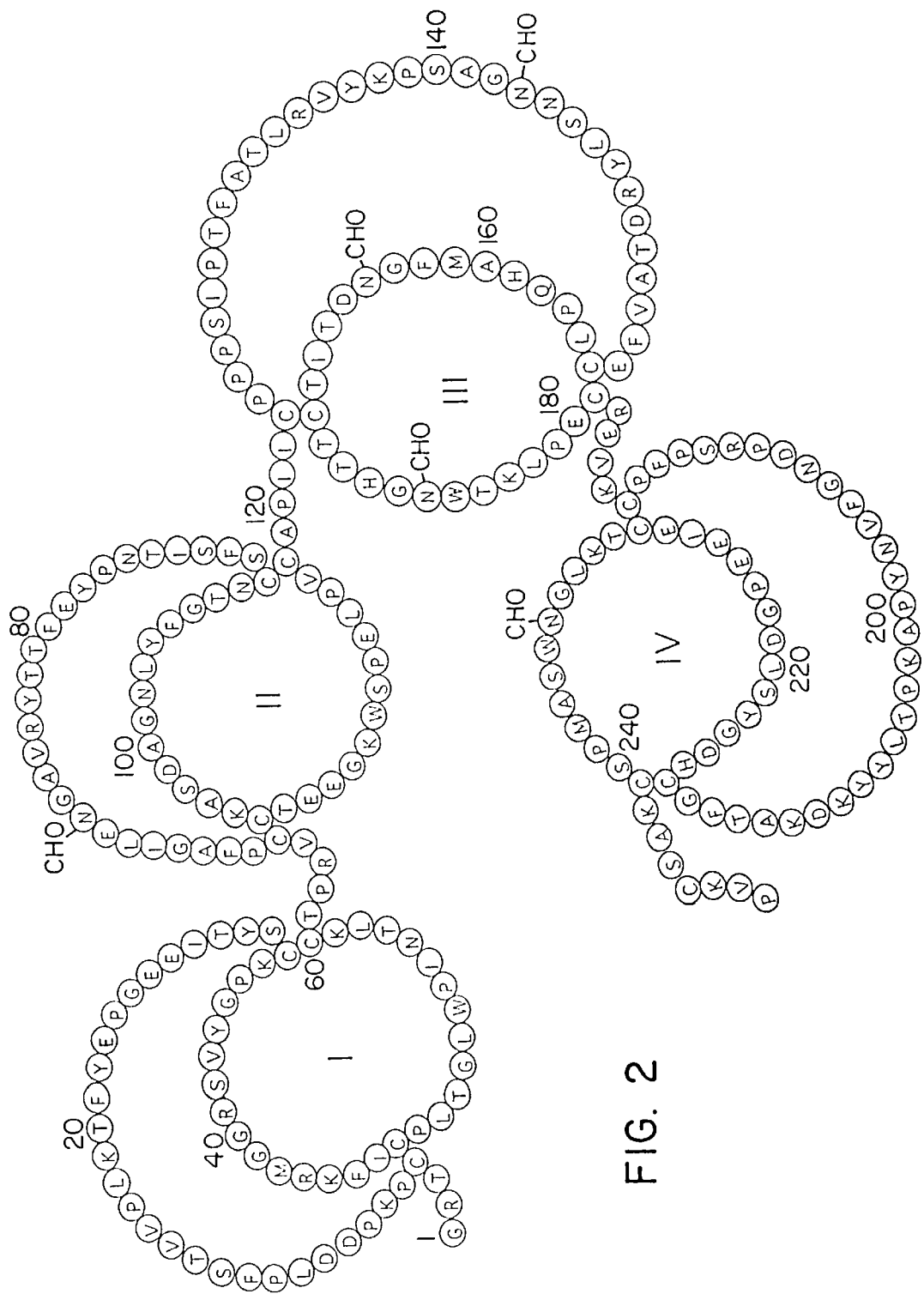
FIG. 2 shows a primary structure of a domain deleted mutant protein (I–IV) and the location of each domain therein (Seq. ID No. 2).

The amplified and cloned DNA fragment is designated as DI-IV gene (FIG. 2).

Figure 3:
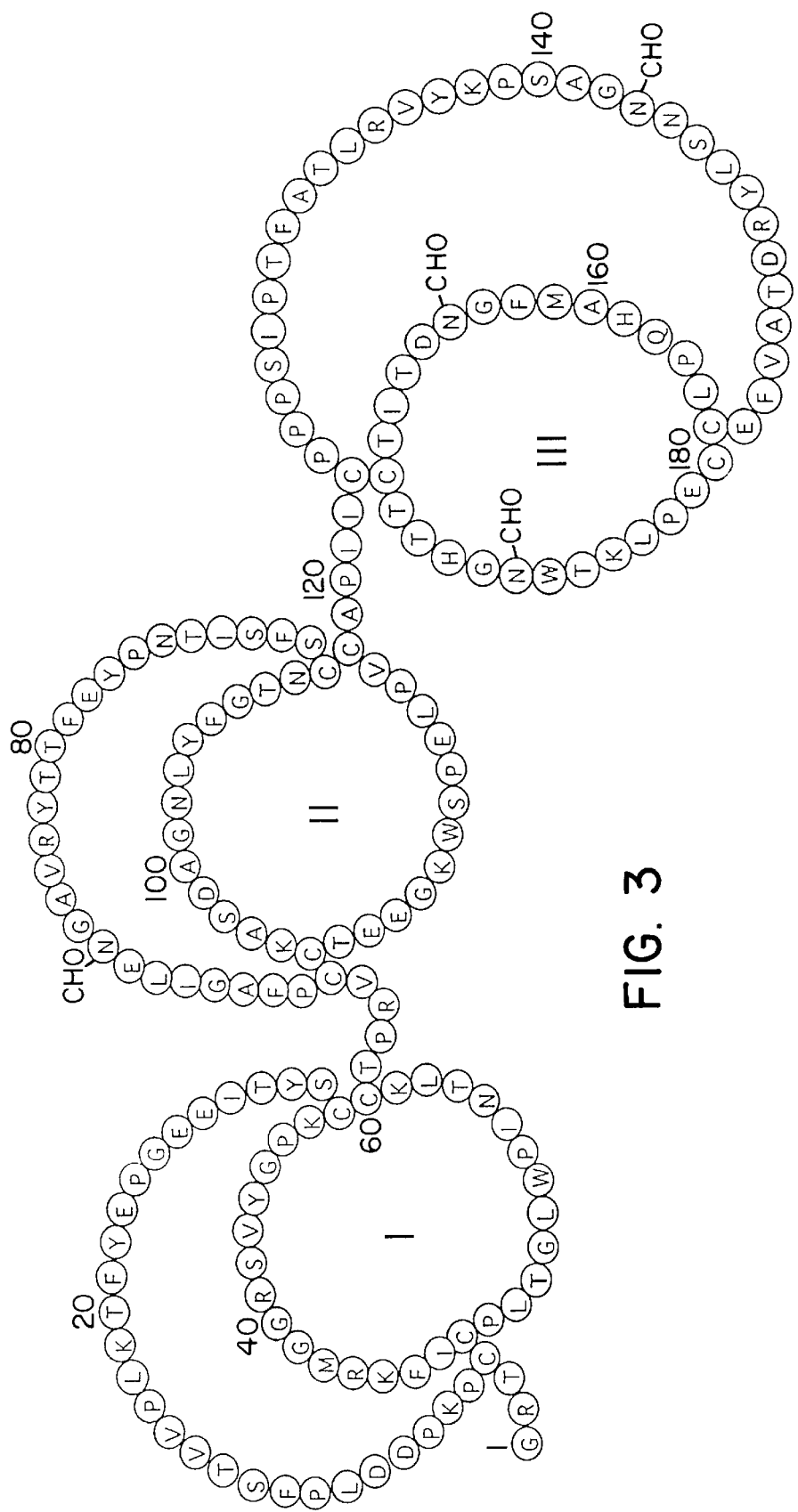
FIG. 3 shows a primary structure of a domain deleted mutant protein (I–III) and the location of each domain therein (Seq. ID No. 3).

By changing the 3'-primer used, a gene lacking a domain different from the above domain may be prepared. For example, using a 3'-primer having the following nucleotide sequence which is prepared by incorporating a termination codon and EcoRI site into the sequence from nucleotide +583 to nucleotide +612, a gene lacking both domains IV and V (DI-III gene, FIG. 3) was prepared in the same way as described above.

5'-TTTGA ATTCT CAGCA TTCTG GTAAT
    TTAGT-3' (SEQ ID NO:9)

(2) Preparation of a Gene Lacking a Domain at the N-Terminal Region

A gene lacking a domain at the N-terminal region may also be prepared in the same way as in the gene lacking a domain at the C-terminal region. However, when the N-terminal gene is simply deleted, a leader sequence for secretion is also lost. Accordingly, for expressing and secreting the objective protein, it is required to ligate a DNA fragment encoding the leader sequence with a gene fragment lacking the N-terminal domain in such a manner that the leader sequence is arranged in agreement with the gene fragment in the reading frames of the amino acids.

Firstly, the DNA fragment encoding a leader sequence is prepared by PCR The DNA fragment may be prepared by quite the same procedure as that of preparing the gene lacking the C-terminal domain. That is, the same 5'-primer as used hereinabove was employed for PCR. As a 3'-primer, the primer having the following sequence which was prepared by incorporating EcoRI site into a sequence complementary to the region (nucleotide +49 to nucleotide +72) from the leader sequence to domain I.

5'-GGGAG AATTC CGTCC TGCAA TAGC-3' (SEQ ID NO: 10)

PCR was performed using each primer to amplify the fragment containing the leader sequence. The objective DNA fragment was then purified and cloned into pUC118, as described above.

In preparing the gene lacking N-terminal domain by PCR, a β2-GPI cDNA cloned into pUC118 was used as a template. As a 3'-primer, the primer having the following sequence which is the outer sequence of a multicloning site, HindIII site.

5'-CCCAG TCACG ACGTT GTAAA-3'    (SEQ ID NO:11)

M13 Primer or an universal primer which is usually used for nucleotide sequencing has the same sequence as described above, and may also be used in the present invention.

A 5'-primer was designed utilizing a sequence in the region from a domain to be deleted to the next domain, and prepared by introducing a EcoRI site so that the signal sequence is arranged in agreement with the gene lacking the N-terminal domain in the reading frames of amino acids. The domains to be expressed, the nucleotide sequences of 5'-primers, and the location of the nucleotide sequences utilized are as described below.

Figure 4:
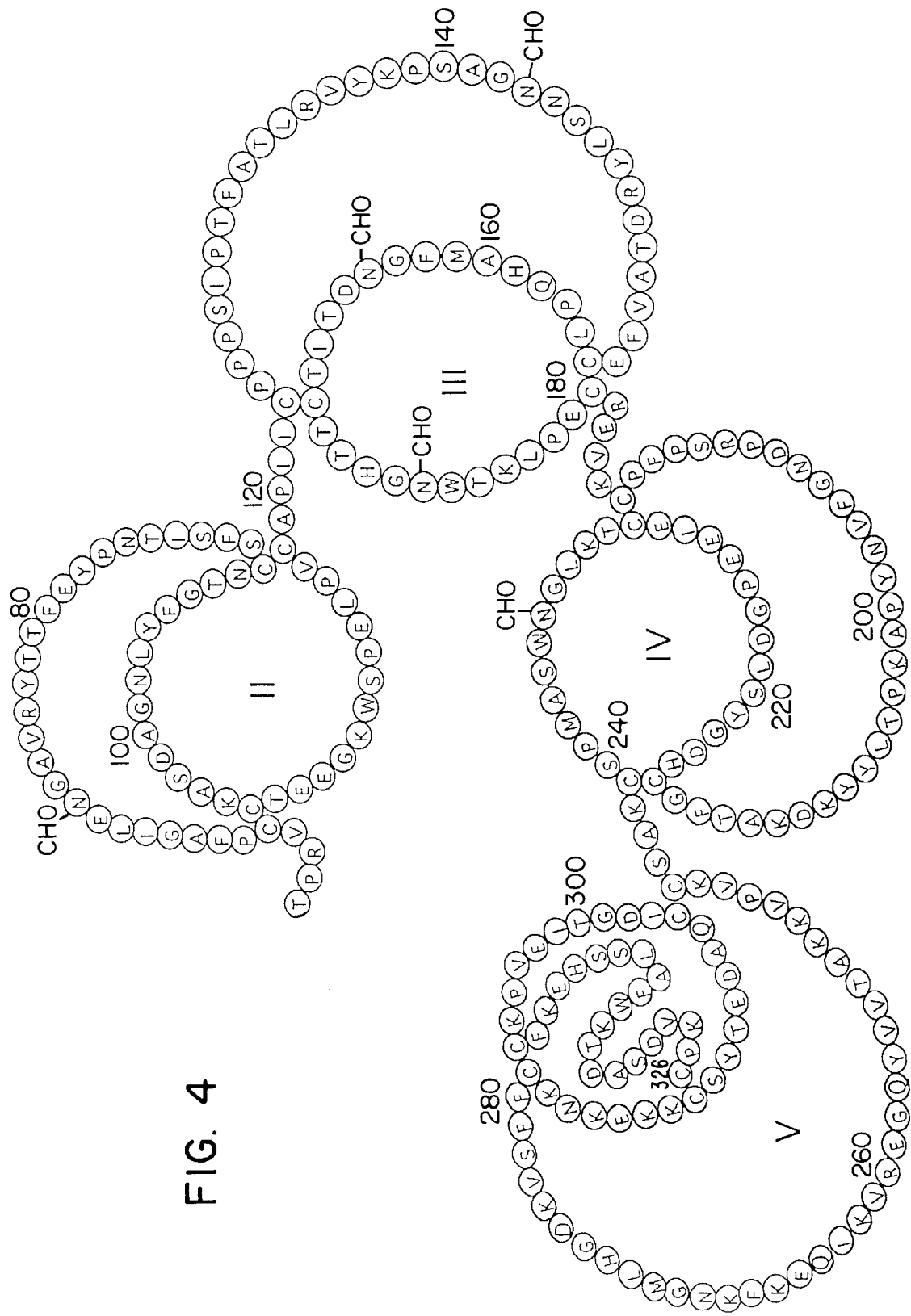
FIG. 4 shows a primary structure of a domain deleted mutant protein (II–V) and the location of each domain therein (Seq. ID No. 4).
Figure 5:
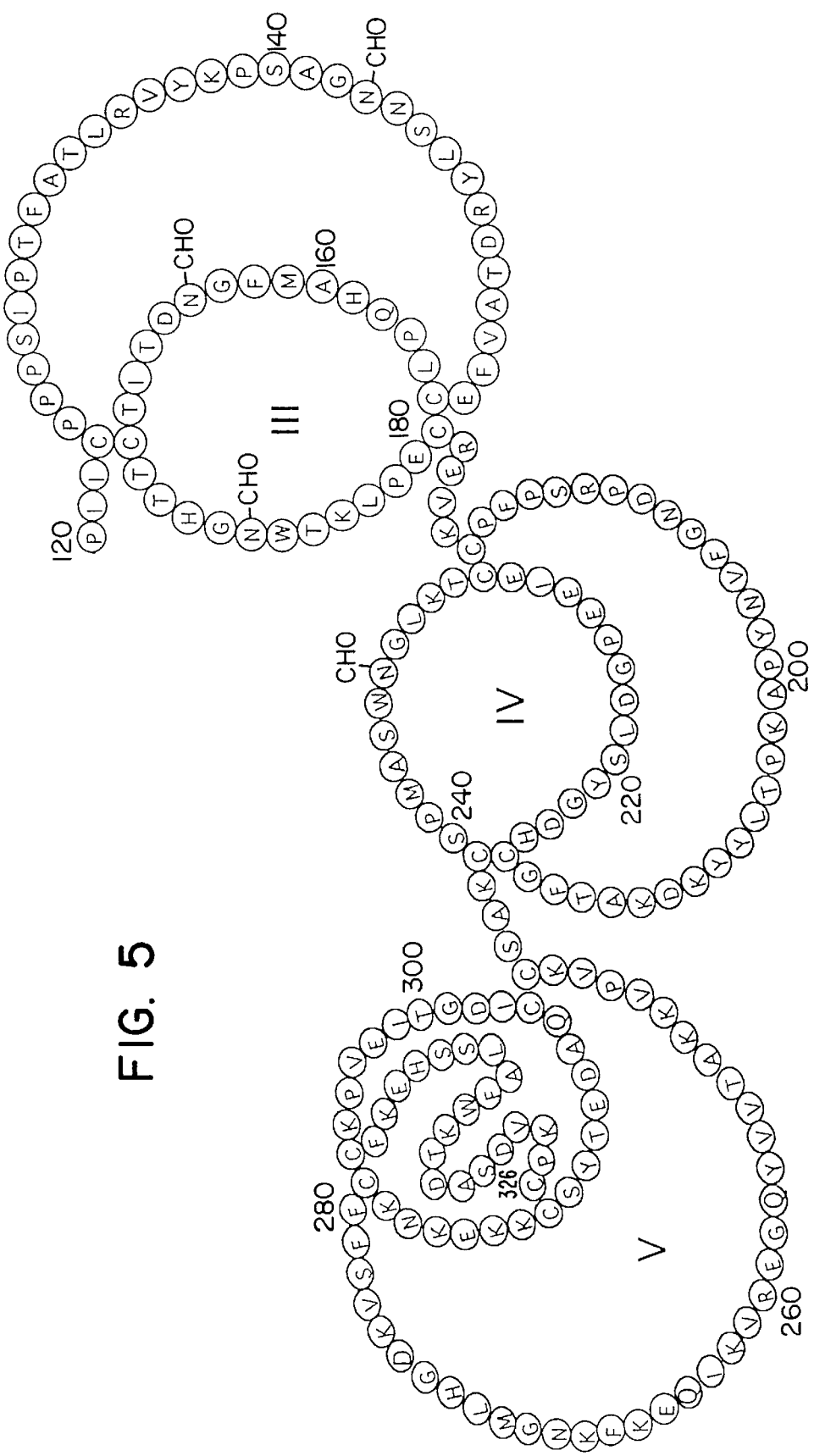
FIG. 5 shows a primary structure of a domain deleted mutant protein (III–V) and the location of each domain therein (Seq. ID No. 5).
Figure 6:
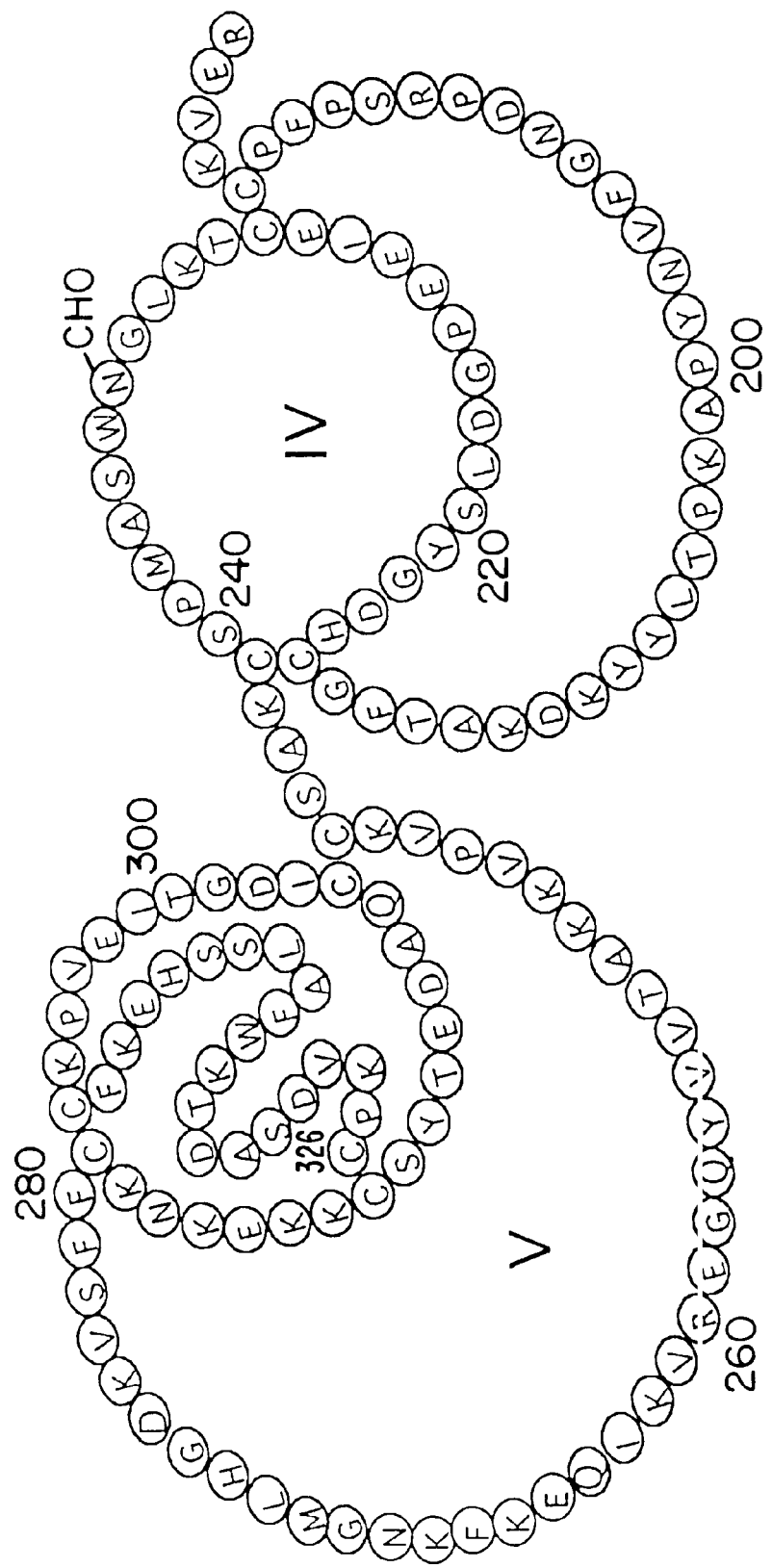
FIG. 6 shows a primary structure of a domain deleted mutant protein (IV . V) and the location of each domain therein (Seq. ID No. 6).

Gene lacking domain I (DII-V gene, FIG. 4) 5 -ACTCT GAATT CTACA CCCAG AGTAT GT-3'(SEQ ID NO;12) (nucleotide +226 to nucleotide +252);

Gene lacking domain I and II (DIII-V gene, FIG. 5);
5'-GTCTG GAATT CCATC ATCTG CCCTC CA-3'(SEQ ID NO: 13) (nucleotide +406 to nucleotide +432);

Gene lacking domain I, II and III (DIV-V gene, FIG. 6);
5'-CCGAA TTCCA GGGAA GTAAA ATGCC CA-3' (SEQ ID NO: 14) (nucleotide +592 to nucleotide +618).

After PCR was carried out using the 5'- and 3'-primers as described above, the objective DNA fragment was recovered, purified and cloned into pUC118, in quite the same way as described above.

(3) Preparation of Gene Lacking N-Terminal and C-Terminal Domains

A gene lacking domain I and domain V was prepared using DII-V gene as a template, according to the procedures similar to those of preparing the gene lacking the C-terminal domain. That is, the gene was prepared by carrying out PCR using as a template pVLD25 as described hereafter and using the same 5'- and 3'-primers as those used for preparing DII-V gene as described above. The prepared gene is designated as DII-IV gene.

(4) Insertion of Each the Deleted Gene into a Transfer Vector

In order to transfect each the domain deleted gene into a baculovirus and express it therein, the objective gene is cut out from pUC118 and cloned again into a transfer vector pVL1393 (pharmingen).

That is, in the case of the genes lacking the C-terminal domain (DI-IV and DI-III genes), the primers used were designed so that the objective gene may be cut out with BamHI and EcoRI. Therefore, pUC118 was digested with those restriction enzymes to obtain the objective fragment, which was then recovered and purified by agarose electrophoresis. The purified fragment was inserted into a transfer vector pVL1393 between the BamHI and EcoRI sites. The constructed recombinant plasmids from DI-IV and DI-III are designated as pVLD14 and pVLD13, respectively.

In the case of the genes lacking the N-terminal domain (DII-V, DIII-V and VIV-V genes), firstly a fragment containing a leader sequence was transferred to pVL1393. That is, since the leader sequence-containing fragment was also designed so that it may be cut off with BamHI and EcoRI, the fragment was cut out and inserted into pVL1393 between the BamHI and EcoRI sites. The obtained plasmid is designated as pVLLS1. Secondly, since the genes lacking the N-terminal domain (DII-V, DIII-V and DIV-V genes) was designed so that it may be cut off with EcoRI and BamHI as described above and so that the domain deleted gene was arranged in agreement with the leader sequence in the reading frames of amino acids, the fragment was cut off with EcoRI and BamHI, after which the fragment was recovered and purified by agarose electrophoresis. The purified fragment was inserted into pVLLS1 between the EcoRI and BglII sites. The constructed recombinant plasmids from DII-V, DIII-V and DIV-G genes are designated as pVLD25, pVLD35 and pVLD45, respectively.

In the case of the gene lacking the N- and C-terminal domain (DII-IV gene), a fragment containing the deleted gene together with the leader sequence may be cut out with BamHI. Accordingly, the fragment was cut off with the restriction enzyme, and the objective DNA fragment was recovered and purified by agarose electrophoresis. The purified fragment was inserted into pVL1393 between the BamHI and BglII sites. The constructed plasmid is designated as pVLD24.

Each of plasmids pVLD13, 14, 25, 35, 45 and 24 was co-transfected together with a baculovirus into an insect cultured cell Sf9 (*Spodoptera frugiperda* cell: available from Pharmingen). Three days after transfection, a recombinant virus was selected by screening the culture supernatant according to a plaque assay. That is, firstly the supernatant was diluted to 10-fold, 100-fold and 1000-fold, respectively. Each dilution was inoculated on $1\times10^6$ insect cells in a dish having a 35 mm diameter. After being adsorbed for an hour, the viral solution was discarded, and 2 ml of an overlay agar medium was replenished. The agar medium was prepared by dissolving a low melting point agar (Sea Plaque) in distilled water in a 3% concentration, sterilizing the aqueous solution and diluting it with 10% FBS-supplemented culture medium to 1% concentration. After the overlay agar medium was solidified, 1 ml of the culture medium was further overlaid thereon.

After culturing at 27° C. for 3 days, to the cells was added 1.0 ml of PBS supplemented with 0.01% neutral red and 4% 5-bromo-4-chloro-3-indolyl-β-D-galactoside (X-gal to stain the cells, resulting in that the plaques were made more detectable. The non-recombinant virus plaques produced β-galactosidase to assume a blue color, whereas the recombinant virus plaques assumed a white color because the gene encoding β-galactosidase has been replaced with the domain deleted gene. The white plaque, which were considered to be the recombinant virus, were further subjected to a plaque assay three times to obtain the purified clone. This recombinant virus was transfected into $1\times10^7$ Sf cells in multiplicity of infection (M.O.I) of 10, followed by incubation in a 75 ml volume plastic flask for 72 hours containing Grace medium supplemented with 10% calf fetal serum.

After the incubation, the culture medium was centrifuged at 5000×g to obtain the supernatant. 50 μl PBS and 50 μl buffer solution for electrophoresis, followed by heating at 100° C. for 10 minutes to prepare the cell extract. The supernatant (10 μl) and the cell extract (10 μl) were subjected to SDS-PAGE (polyacrylamide gel electrophoresis). After the electrophoresis, staining with Coomassie Brilliant Blue (CBB) and Western blotting using anti-β2-GPI antiserum were performed to confirm whether the domain deleted mutant protein was produced.

The results of the staining analysis with CBB revealed that the samples, which were prepared from the cells transfected with the recombinant viruses having the β2-GPI domain-deleted genes, DIV-V, DIII-V, DII-V, DI-III and DI-IV genes, inserted therein, showed specific bands indicating about 20, 35, 38, 30 and 38 Kilodalton, whereas the samples from the cells transfected with the wild type baculovirus did not show such specific bands. Furthermore, the results of Western blotting revealed that an anti-β2-GPI antiserum reacted only with bands which appeared specifically from the samples of the cells transfected with the recombinant virus having the domain deleted gene inserted therein. From those results, it was confirmed that the detected proteins were the desired domain deleted mutant proteins.

After the recombinant virus had been transfected into an insect cell, an aliquot was collected from the culture medium of the transfected cells at intervals of a predetermined time period, and analyzed by Western blotting for a change with the passage of time in production of the domain deleted mutant proteins. As a result, it was confirmed both in the supernatant and cell extract that the domain deleted mutant proteins were produced 24 hours after the beginning of the culture, and that the amount of the proteins produced reached the maximum 60 to 72 hours after the beginning of the culture.

(5) Purification of the β2-GPI Domain-Deleted Mutant Proteins Produced in Insect Cells Transfected with the Recombinant Baculovirus The β2-GPI domain-deleted mutant proteins were purified from the culture supernatant of the insect cell transfected with the recombinant baculovirus by an affinity column chromatography using an anti-β2-GPI monoclonal antibody.

That is, an affinity column, wherein 5 mg of a mouse anti-β2-GPI monoclonal antibody Cof20 or Cof23 (WO 092/19755) was bound to 5 ml of SEPHAROSE CL4resin (a granule composed of agarose gel and used as a carrier for affinity chromatography) (Pharmacia Inc.), was prepared in a conventional manner. The recombinant virus was transfected into 1×10$^8$ Sf cells in M.O.I. of 10, which was then cultured in a serum free medium (Sf-900, Gibco Inc.) for 72 hours. After 100 ml of the resulting supernatant was dialyzed overnight against 2 liters of 50 mM sodium chloride-containing 10 mM phosphate buffer (PBS, pH 7.4), the obtained dialysate was applied to the affinity column previously equilibrated with the same buffer, whereby the protein was bound to the antibody on the affinity column. In the case of DIV-V, a monoclonal antibody Cof23-bound affinity column was used. For the other domain deleted proteins (DIII-V, DII-V, DI-III and DI-IV), a monoclonal antibody Cof20-bound affinity column was used.

The column was then washed with a sufficient amount of the same buffer. The protein was eluted with glycine hydrochloride buffer, pH 2.5, and recovered. The recovered protein fraction was immediately dialyzed overnight against 2 liters of PBS, pH 7.4, and the obtained dialysate was concentrated through a dialysis tube using 40% polyethylene glycol (PEG) solution. After concentrated, the condensate was dialyzed overnight against 2 liters of 150 mM sodium chloride-containing HEPES buffer, pH 7.2. The obtained protein was regarded as a purified product.

Figure 7:
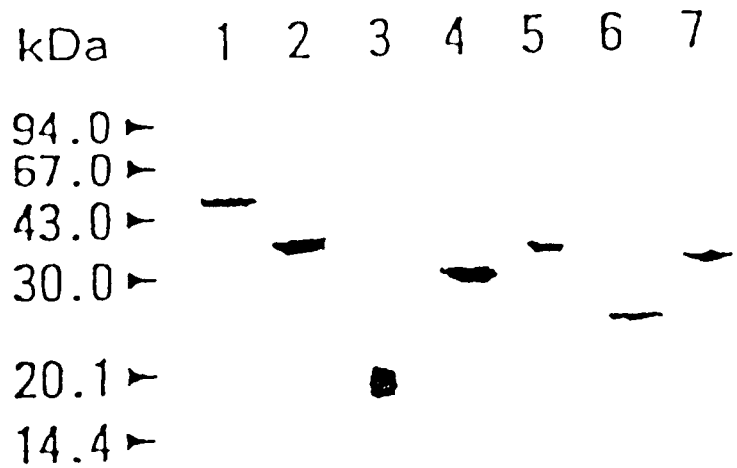
FIG. 7 shows results from an analysis according to SDS-polyacrylamide gel electrophoresis (Coomassie Blue staining) for a purified specimen of each domain deleted mutant protein obtained according to the method of the present invention.
Figure 8:
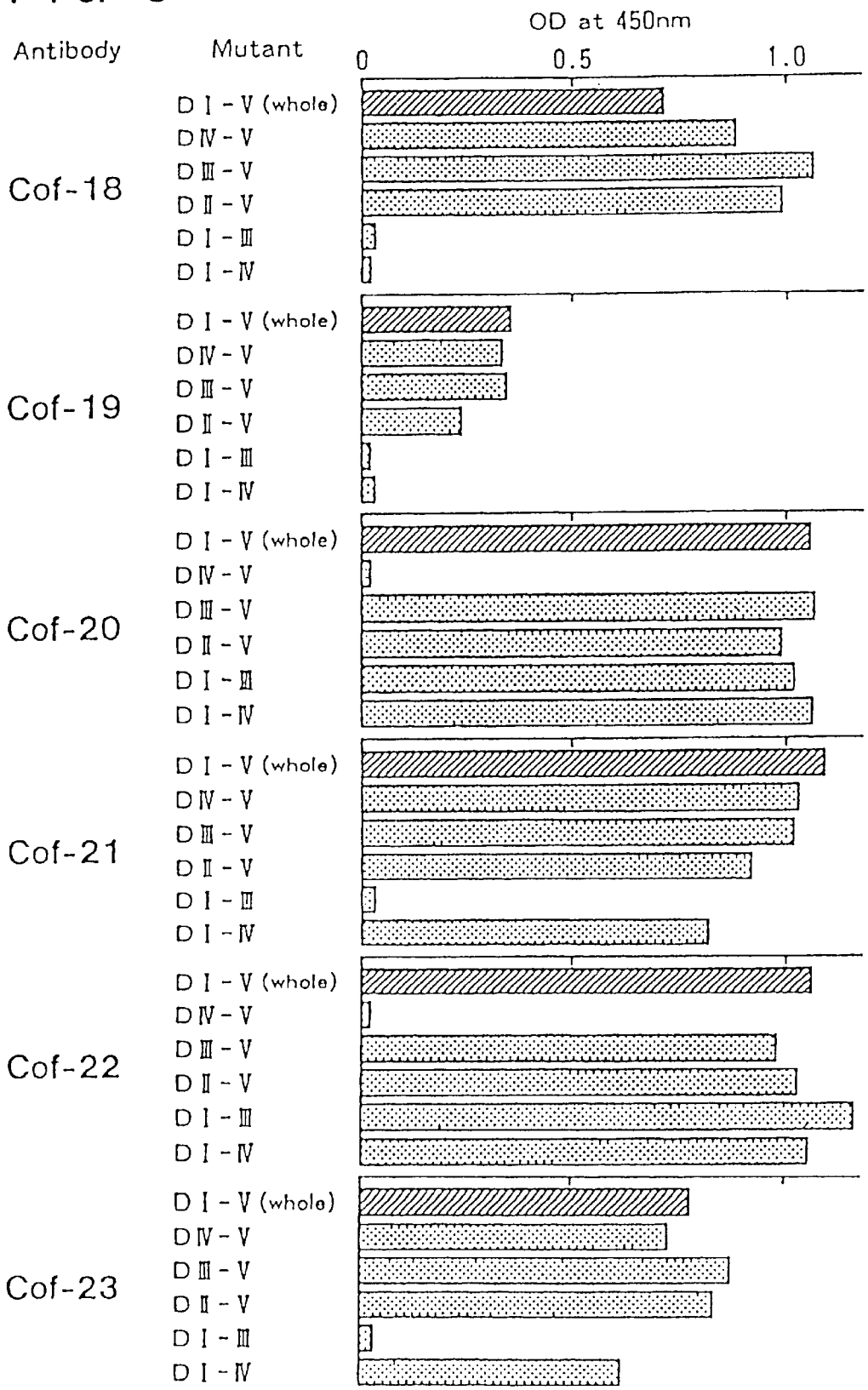
FIG. 8 shows results from a comparison in the reactivity between each domain deleted mutant protein obtained according to the method of the present invention and a mouse anti-human β2-GPI monoclonal antibody, according to ELISA.

The purified product of each domain deleted mutant protein produced was analyzed by SDS-PAGE (Coomassie Blue staining). The results showed that those proteins were purified at an extremely high purity of 95% or more (FIG. 7), indicating that the affinity column chromatography was extremely effective for purifying the proteins. Furthermore, the results from SDS-PAGE analysis also showed that each domain deleted mutant protein has the molecular weight as shown in Table 1 below.

TABLE 1

Molecular weight of each domain deleted protein

| | Molecular Weight (kDa) |
|---|---|
| DIV-V | 18.9 |
| DIII-V | 32.7 |
| DII-V | 34.5 |
| DI-III | 25.6 |
| DI-IV | 36.4 |

(6) Analysis of an Epitope for an Anti-β2-GPI Monoclonal Antibody Using the Domain Deleted Mutant Protein Fifty μl of each solution (10 μg/ml) of the various obtained domain deleted mutant proteins (DIV-V, DIII-V, DII-V, DI-III and DI-IV) and a recombinant protein containing all domains (DI-V (whole)) was charged in each well of a 96-well microtiter plate (S-Plate, Sumitomo Bakelite Co., Ltd.), followed by incubation at 4° C. overnight. After washing three times with 200 g of Tween 20-supplemented phosphate buffered saline (PBS-Tween, pH 7.4) (a non-ionic surtactant), 200 μl of 3% gelatin solution was charged in each well, and then allowed to stand at room temperature for one hour.

After the gelatin solution was removed, 100 μl of a 0.2 μg/ml solution of each purified anti-β2-GPI monoclonal antibody (Cof-18, Cof-19, Cof-20, Cof-21, Cof-22 and Cof-23) was charged in each well, and then allowed to stand at room temperature for an hour. After washing three times with 200 μl of PBS-TWEEN, 100 μl of a peroxidase-labeled anti-mouse IgG antibody was charged in each well, and then allowed to stand at room temperature for an hour. After washing in the same way as described above, 100 l of a color developer (0.3 mM tetramethylbenzidine, 0.0003% $H_2O_2$) was added to be reacted for just 10 minutes. The reaction was terminated by adding 100 μl of 2N $H_2SO_4$, and absorbance was measured at 450 nm.

The results are shown in FIG. 8. Based on the results, an epitope for each purified anti-β2-GPI monoclonal antibody was analyzed, and the results obtained are shown in FIG. 9. By the use of the domain deleted mutant proteins in such a manner, an epitope for each anti-β2-GPI antibody can be readily analyzed.

(7) Analysis of an Epitope for Each of a Monoclonal Anti-Cardiolipin Antibody (Anti-CL Antibody: WB-CAL-1, J. Immunol., 149, 1063–1068 (1992) and an Autoantibody in Serum From Patient With Antiphospholipid Syndrome, Using the Domain Deleted Mutant Protein, and Detection of the Autoantibody Method 1:

Fifty μl of each solution (10 μg/ml) of a recombinant β2-GPI protein containing all domains (DI-V (whole)) and the various domain deleted mutant proteins as obtained herein above (DIV-V, DIII-V, DII-V, DI-III and DI-IV) was charged in each well of a 96-well microtiter plate (S-Plate and C-Plate, Sumitomo Bakelite Co., Ltd.), followed by incubation at 4° C. overnight. C-Plate is a plate prepared by chemically introducing carboxyl groups on the surface of S-Plate. After washing three times with 200 μl of PBS-Tween, 200 μl of 3% gelatin solution was charged in each well, and then allowed to stand at room temperature for an hour.

After the gelatin solution was removed, 100 μl of a purified monoclonal anti-cardiolipin antibody (anti-CL antibody: WB-CAL-1) appropriately diluted or 100 μl of a positive serum from a patient with antiphospholipid syndrome was charged in each well, and then allowed to stand at room temperature for an hour. After washing three times with 200 μl of PBS-TWEEN, 100 μl of a peroxidase-labeled anti-mouse IgG antibody or an anti-human IgG antibody was charged in each well, and then allowed to stand at room temperature for an hour. After washing in the same way as described above, 100 μl of a color developer (0.3 mM tetramethylbenzidine, 0.0003% $H_2O_2$) was added to be reacted for just 10 minutes. The reaction was terminated by adding 100 μl of 2N $H_2SO_4$, and absorbance was measured at 450 nm.

Figure 10:
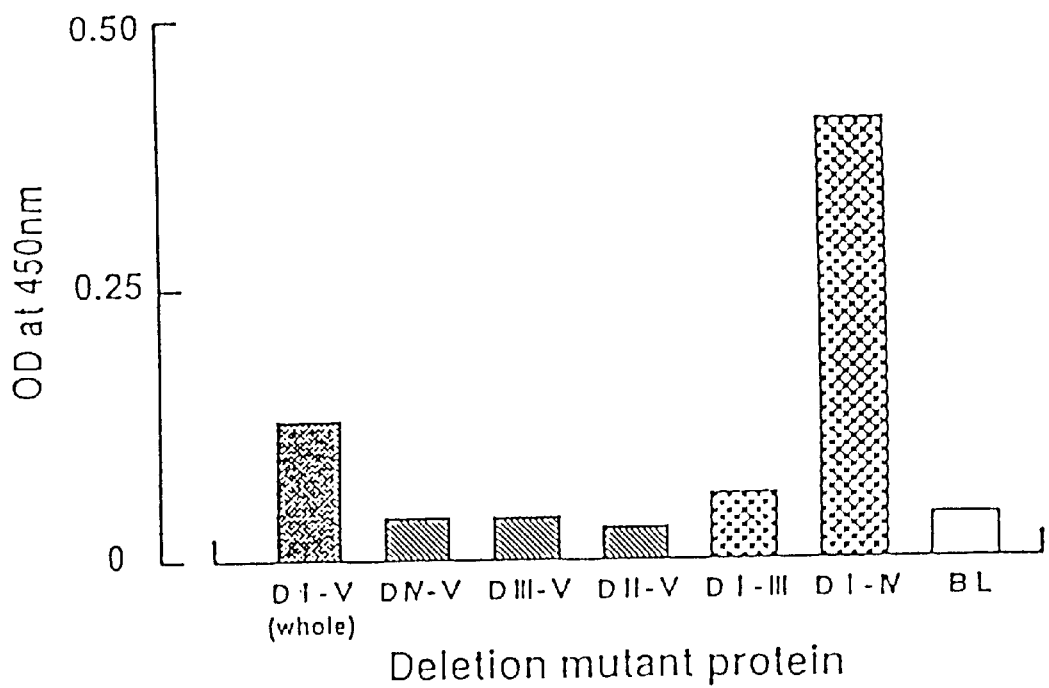
FIG. 10 shows results from an analysis for an epitope for an anticardiolipin antibody (anti-CL antibody), according to ELISA using each domain deleted mutant protein and an S-plate.
Figure 11:
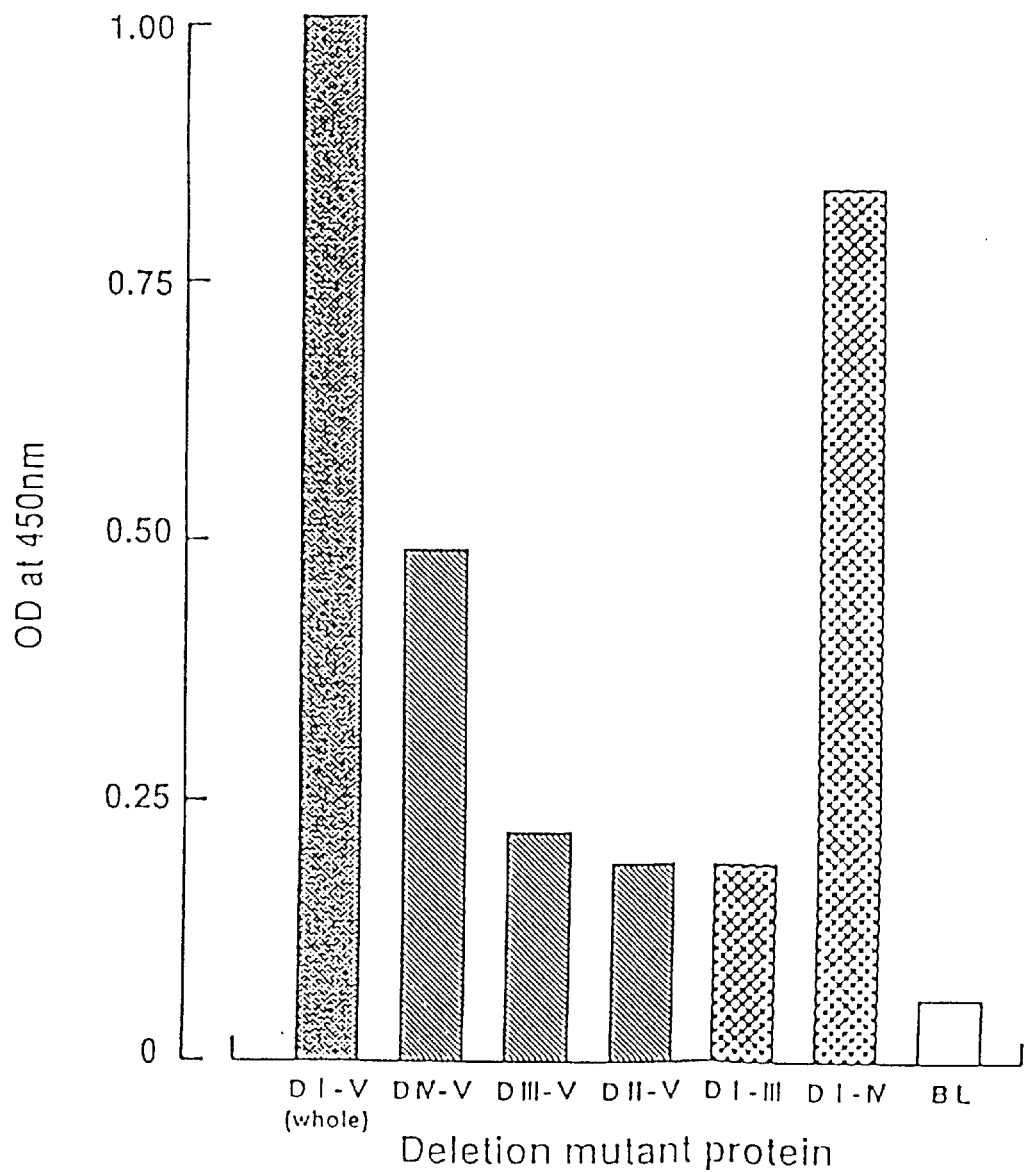
FIG. 11 shows results from an analysis for an epitope for an anti-CL antibody, according to ELISA using each domain deleted mutant protein and a C-plate.

The results from the measurements on S-Plate and C-Plate using the purified monoclonal anticardiolipin antibody (anti-CL antibody) are shown in FIGS. 10 and 11, respectively. In addition, the results from the measurements on S-Plate and C-Plate using three sera from patients with syphilis, four normal sera, three sera from patients with SLE and are shown in FIGS. 12 to 14 and FIGS. 15 to 17, respectively.

The results showed that, when the domain deleted mutant proteins were bound to the plate without carboxyl groups introduced (S-Plate), only the domain deleted mutant protein lacking domain V and containing domain IV enabled the measurement of anti-CL antibody (FIG. 10). On the other hand, when bound to the plate having carboxyl groups introduced thereon (C-Plate), the domain deleted mutant proteins containing domain IV and V enabled the measurement of anti-CL antibody (FIG. 11), similarly to the case when a human serum-derived β2-GPI bound to the plate is used. Even DI-IV protein lacking domain V enabled the measurement of anti-CL antibody on the plate having carboxyl groups introduced thereon (FIG. 11). It was thus confirmed that the mutant protein containing at least domain IV is effective for the determination of anti-CL antibody.

In the case that human sera were assayed, the sera from patients with SLE showed the same results as anti-CL antibody (FIG. 16). However, no characteristic binding of an antibody was observed for any of the sera from normal persons and patients with syphilis.

Method 2:

Fifty μl of a 50 μg/ml solution of a bovine heart-derived cardiolipin in ethanol was charged in each well of a 96-well microtiter plate (Immulon-1, Dynatech Co., Ltd.) and dried under reduced pressure. After washing in the same manner as described hereinbefore, 100 μl of each solution (10 μg/ml) of the recombinant β2-GPI protein containing all domains (DI-V (whole)) and the domain deleted mutant proteins (DIV-V, DIII-V, DII-V, DI-III and DI-IV) was charged in each well, and then allowed to stand at room temperature for an hour. After washing, 100 μg of anti-cardiolipin antibody (anti-CL antibody) appropriately diluted was charged in each well to be reacted for 30 minutes. After washing, 100 μl of a peroxidase-labeled antimouse IgG antibody or an anti-human IgG antibody was charged in each well, and then allowed to stand at room temperature for an hour. After washing in the same manner as described above, 100 μl of a color developer (0.3 mM tetramethylbenzidine, 0.0003% $H_2O_2$) was added to be reacted for just 10 minutes. The reaction was terminated by adding 100 μl of 2N $H_2SO_4$, and absorbance was measured at 450 nm.

Figure 18:
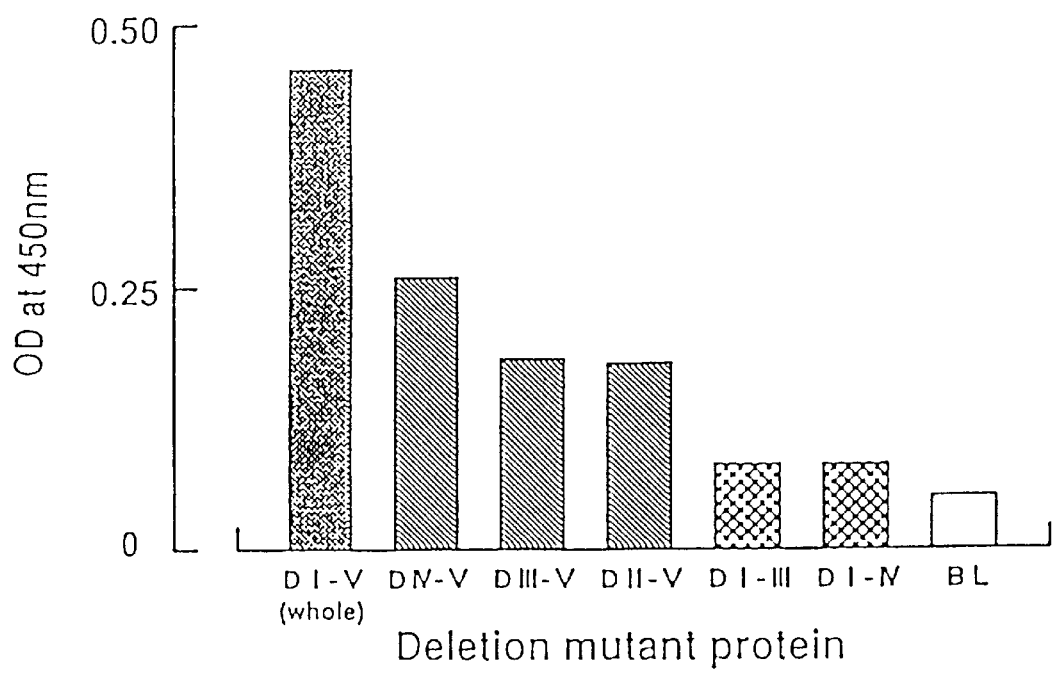
FIG. 18 shows results from an analysis for an epitope in β2-GPI for an anticardiolipin antibody, according to ELISA using each domain deleted protein and a cardiolipin-immobilized solid phase plate.

The results obtained are shown in FIG. 18. As a result, when the domain deleted mutant proteins were used in the system of ELISA using a cardiolipin (aCL-ELISA), the binding of anti-CL antibody was observed for the domain deleted mutant proteins containing at least domain V and IV (FIG. 18). Accordingly, it was confirmed that the domain deleted protein containing domain V and IV enabled the measurement of anti-CL antibody in the aCL-ELISA system.

(8) Analysis of a Phospholipid (Cardiolipin) Binding Site in β2-GPI

Method 1:

Fifty μl of a 50 μg/ml solution of a bovine heat-derived cardiolipin in ethanol was charged in each well of a 96-well microtiter plate (Immulon-1, Dynatech Co., Ltd.), and dried under reduced pressure. After washing in the same manner as described hereinbefore, 100 μl of each solution (10 μg/ml) of the recombinant β2-GPI protein containing all domains (DI-V (whole)) and the domain deleted proteins (DIV-V, DIII-V, DII-V, DI-III and DI-IV) was charged in each well, and then allowed to stand at room temperature for an hour. After washing, 100 μl of an anti-β2-GPI antibody appropriately diluted was charged in each well to be reacted for 30 minutes. After washing, 100 μl of a peroxidase-labeled anti-mouse IgG antibody or a peroxidase-labeled anti-human IgG antibody was charged in each well, and then allowed to stand at room temperature for an hour. After washing in the same manner as described above, 100 μl of a color developer (0.3 mM tetramethylbenzidine, 0.0003% $H_2O_2$) was added to be reacted for just 10 minutes. The reaction was terminated by adding 100 μl of 2N $H_2SO_4$, and absorbance was measured at 450 nm.

Figure 19:
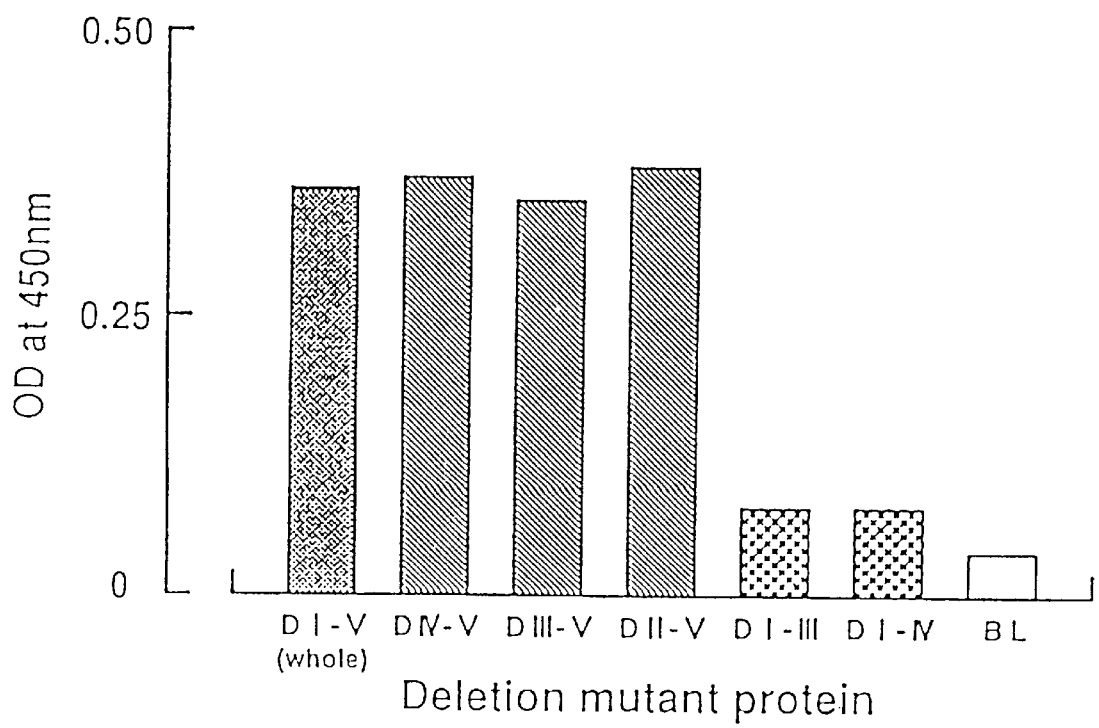
FIG. 19 shows results from an analysis for a cardiolipin binding site in β2-GPI, according to ELISA using each domain deleted mutant protein, a cardiolipin-immobilized solid phase plate and an anti-β2-GPI antibody.

The results are shown in FIG. 19. The results showed that among the domain deleted mutant proteins used, only the protein containing domain V could be bound to a phospholipid (cardiolipin).

Method 2:

Fifty μl of a 50 μg/ml solution of a bovine heart-derived cardiolipin in ethanol was charged in each well of a 96-well microtiter plate (Immulon-1, Dynatech Co., Ltd.), and dried under reduced pressure. After washing in the same manner as described hereinbefore, each solution (0 to 50 μg/ml) of the recombinant β2-GPI protein containing all domains (DI-V (whole)) and the domain deleted mutant proteins (DIV-V, DIII-V, DII-V, DI-III and DI-IV), serving as an inhibitor, was incubated with 5 μg/ml of a biotinated human serum-derived β2-GPI (100 μl in total/well) at room temperature for an hour. After washing, 100 μl of an avidinated peroxidase was charged in each well to be reacted for 15 minutes. After washing, 100 μl of a color developer (0.3 mM tetramethylbenzidine, 0.0003% $H_2O_2$) was added to be reacted for just 10 minutes. The reaction was terminated by adding 100 μl of 2N $H_2SO_4$, and absorbance was measured at 450 nm.

The results are shown in FIG. 20. It was confirmed by the results that the domain deleted protein containing domain V strongly inhibited the binding of the biotinated human serum-derived β2-GPI to the phospholipid.

From the results of the foregoing analyses, it was confirmed that:

(1) the phospholipid binding site in β2-GPI is present in the fifth domain (domain V);
(2) the epitope (an antibody recognition site) which is recognized by the autoantibody from patients with antiphospholipid syndrome is present in a region centering around the fourth domain (domain IV);
(3) this epitope is usually cryptic, but domain V binds to phospholipid or the like, resulting in that the mutant protein undergoes a conformational change, whereby the epitope is exposed to be recognized by the autoantibody.

INDUSTRIAL APPLICABILITY

By using a polypeptide containing a specific domain(s) of β2-GPI, only an autoantibody (an anti-carbiolipin antibody) from patients with antiphospholipid syndrome can be specifically assayed, without being affected by an anti-cardiolipin antibody from patients with infectious disease. Such a characteristic feature is extremely advantageous, as compared to the prior art assay method in which the two antibodies from antiphospholipid syndrome and infectious disease can be differentially assayed quantitatively only when two determinations are conducted under the two conditions, i.e., in the presence and absence of β2-GPI.

---

We claim:

1. A method for assaying an autoimmune anticardiolipin antibody in a sample which comprises:

contacting said sample with a complex consisting essentially of a polypeptide comprising at least domain IV of a human β2-glycoprotein I but lacking any one or more of domains I–III and V of the human β2-glycoprotein I, said complex bound to a phospholipid or a polar group, and detecting said autoimmune anticardiolipin antibody bound to the complex.

2. The method according claim 1, wherein said polypeptide further comprises domain V of the human β2-glycoprotein I.

3. The method according to claim 2, wherein said polypeptide is immobilized on a carrier to form a solid phase reagent.

4. The method according to claim 3, wherein said carrier has said phospholipid bound thereto.

5. The method according to claim 3, wherein said carrier has said polar group bound thereto.

6. The method according to claim 3, wherein said detecting step comprises contacting a labeled anti-immunoglobulin antibody to said contacted solid phase reagent and measuring label bound to said complex.

7. The method according to claim 6, wherein said anti-immunoglobulin antibody is enzyme labeled.

8. The method according to claim 1, wherein said phospholipid or said polar group is bound to a carrier.

9. A kit comprising:

a) a complex reagent consisting essentially of a polypeptide comprising at least domain IV of a human β2-glycoprotein I but lacking any one or more of domains I–III and V of the human β2-glycoprotein I, said complex bound to a phospholipid or a polar group, and b) a reagent for detecting autoimmune anticardiolipin antibody bound to said complex reagent.

10. The kit according to claim 9, wherein said polypeptide further comprises domain V of the human β2-glycoprotein I.

11. The kit according to claim 10, wherein said polypeptide is immobilized on a carrier to form a solid phase reagent.

12. The kit according to claim 11, wherein said carrier has said phospholipid bound thereto.

13. The kit according to claim 11, wherein said carrier has said polar group bound thereto.

14. The kit according to claim 9, wherein said phospholipid or said polar group is bound to a carrier.

15. The kit according to claim 9, wherein said reagent is a labeled anti-immunoglobulin antibody.

16. The kit according to claim 15, wherein said anti-immunoglobulin antibody is enzyme labeled.

17. The kit according to claim 16, which further comprises a substrate solution for the enzyme label and a standard antibody solution having a known concentration.

18. The method according to claim 8, wherein said detecting step comprises contacting a labeled anti-immunoglobulin antibody to said contacted solid phase reagent and measuring label bound to said complex.

* * * * *